United States Patent
Savola et al.

(10) Patent No.: US 11,324,732 B2
(45) Date of Patent: May 10, 2022

(54) METHODS FOR THE TREATMENT OF DYSKINESIA IN CEREBRAL PALSY

(71) Applicant: AUSPEX PHARMACEUTICALS, INC., Parsippany, NJ (US)

(72) Inventors: Juha-Matti Savola, Reinach (CH); Mark Forrest Gordon, Jericho, NY (US); Frank Schneider, Berlin (DE)

(73) Assignee: Auspex Pharmaceuticals, Inc., Parsippany, NJ (US)

( * ) Notice: Subject to any disclaimer, the term of this patent is extended or adjusted under 35 U.S.C. 154(b) by 119 days.

(21) Appl. No.: 16/713,917

(22) Filed: Dec. 13, 2019

(65) Prior Publication Data

US 2020/0188371 A1   Jun. 18, 2020

Related U.S. Application Data

(60) Provisional application No. 62/801,450, filed on Feb. 5, 2019, provisional application No. 62/779,232, filed on Dec. 13, 2018.

(51) Int. Cl.
  *A61K 31/4375* (2006.01)
  *A61P 25/14* (2006.01)

(52) U.S. Cl.
  CPC .......... *A61K 31/4375* (2013.01); *A61P 25/14* (2018.01)

(58) Field of Classification Search
  CPC ............................ A61K 31/4375; A61P 25/14
  See application file for complete search history.

(56) References Cited

U.S. PATENT DOCUMENTS

| | | | |
|---|---|---|---|
| 8,524,733 B2 | 9/2013 | Gant et al. | |
| 9,233,959 B2 | 1/2016 | Sommer et al. | |
| 2010/0130480 A1* | 5/2010 | Gant | A61P 21/00 514/220 |
| 2012/0003330 A1* | 1/2012 | Gant | C07C 217/60 424/722 |
| 2016/0287574 A1 | 10/2016 | Stamler et al. | |
| 2018/0263972 A1 | 9/2018 | Zhang et al. | |

FOREIGN PATENT DOCUMENTS

| | | |
|---|---|---|
| CN | 107624067 A | 1/2018 |
| WO | 2016/144901 A1 | 9/2016 |

OTHER PUBLICATIONS

Achenbach et al., "The Child Behavior Checklist and related forms for assessing behavioral/emotional problems and competencies", Pediatr Rev. 2000, 21(8), 265-271.
Achenbach, "Advancing assessment of children and adolescents: commentary on evidence-based assessment of child and adolescent disorders", J. Clin. Child Adolesc. Psychol., 2005, 34, 541-547.
Battini et al., "Movement Disorder-Childhood Rating Scale: reliability and validity", Pediatr. Neurol. 2008, 39(4), 259-265.
Battini et al., "Responsiveness of the MD-Childhood Rating Scale in dyskinetic cerebral palsy patients undergoing anticholinergic treatment", Eur J Paediatr Neurol, 2014, 18(6), 698-703.
Busner et al., "The Clinical Global Impressions Scale: Applying a Research Tool in Clinical Practice", Psychiatry (Edgmont) 2007, 4(7), 28-37.
Cans, "Surveillance of cerebral palsy in Europe: a collaboration of cerebral palsy surveys and registers", Developmental Medicine & Child Neurology, 2000, 42, 816-824.
Chatterjee, et al., "Tetrabenazine in the treatment of severe pediatric chorea", Movement disorders, vol. 18, No. 6, 2003, 703-706.
Chen et al., "Increasing the sample size when the unblinded interim result is promising", Stat Med, 2004, 23(7), 1023-1038.
Chouinard et al., "Manual for the Extrapyramidal Symptom Rating Scale (ESRS)", Schizophrenia Research, 2005, 76, 247-265.
Dumas et al., "Concurrent Validity and Reliability of the Pediatric Evaluation of Disability Inventory Computer Adaptive Test Mobility Domain", Pediatric Physical Therapy, 2012, 24, 171-176.
Heggarty, et al., "Tetrabenazine in athetoid cerebral palsy" Developmental Medicine & Child Neurology, 1974, 16, 137-142.
Huntington Study Group., "Unified Huntington's Disease Rating Scale: reliability and consistency", Huntington Study Group. Mov Disord 1996, 11(2), 136-142.
Johns MW., "The assessment of sleepiness in children and adolescents", Sleep Biol. Rhythm, 2015, 13(Suppl. 1), 97.
Law et al., "The Canadian occupational performance measure: an outcome measure for occupational therapy", Can. J. Occup. Ther., Apr. 1990, 57(2), 8287.
Little et al., "Statistical Analysis with Missing Data", Second Edition, 2002, New York, John Wiley & Sons.
Mehta et al., "Adaptive increase in sample size when interim results are promising: a practical guide with examples", Stat Med, 2011, 30(28), 3267-3284.
Monbaliu et al., "Clinical presentation and management of dyskinetic cerebral palsy", Lancet Neurol., 2017, 16(9), 741-749.
Posner et al., "The Columbia-Suicide Severity Rating Scale: Initial Validity and Internal Consistency Findings From Three Multisite Studies With Adolescents and Adults", American Journal of Psychiatry, 2011, 168(12), 1266-1277.
Varni et al., "The PedsQL™ in pediatric cerebral palsy: Reliability, validity, and sensitivity of the Generic Core Scales and Cerebral Palsy Module", Developmental Medicine and Child Neurology, 2006, 48, 442-449.
Wimalasundera et al., "Cerebral palsy", Pract Neurol, 2016, 16, 184-194.

* cited by examiner

*Primary Examiner* — Timothy R Rozof
(74) *Attorney, Agent, or Firm* — BakerHostetler

(57) ABSTRACT

The disclosure is directed to methods of treating dyskinesia in cerebral palsy in human patients using deutetrabenazine and its active metabolites.

16 Claims, No Drawings

METHODS FOR THE TREATMENT OF DYSKINESIA IN CEREBRAL PALSY

CROSS REFERENCE TO RELATED APPLICATIONS

This application claims the benefit of U.S. Provisional Application Nos. 62/779,232, filed Dec. 13, 2018, and 62/801,450, filed Feb. 5, 2019, the entireties of which are incorporated by reference herein.

TECHNICAL FIELD

The disclosure is directed to methods of treating dyskinesia in cerebral palsy in human patients, including pediatric patients using deutetrabenazine and its active metabolites.

BACKGROUND

Deutetrabenazine ((RR,SS)-1,3,4,6,7,11b-hexahydro-9,10-di(methoxy-d3)-3-(2-methylpropyl)-2H-benzo[a]quinolizin-2-one) is a vesicular monoamine transporter type 2 (VMAT2). The biologically active metabolites formed from deutetrabenazine (alpha-dihydrotetrabenazine [α-HTBZ] and beta-dihydrotetrabenazine [(β-HTBZ]) are potent inhibitors of VMAT2 binding, with inhibition constant values of 3.8 and 22 nM, respectively. Deutetrabenazine exhibits an increased half-life of its active metabolites, relative to tetrabenazine (e.g., U.S. Pat. No. 8,524,733).

Deutetrabenazine is approved by the U.S. Food and Drug Administration under the tradename AUSTEDO® for the treatment of chorea associated with Huntington's disease (HD) and for the treatment of tardive dyskinesia (TD) in adults. Pharmaceutical compositions comprising deutetrabenazine are disclosed in U.S. Pat. No. 9,233,959. U.S. Published Application No. 2016/0287574 discloses deutetrabenazine for the treatment of abnormal involuntary movement disorders.

Cerebral palsy (CP) is a nonprogressive disturbance of brain function that usually occurs in the developing fetal or infant brain (age ≤2 years). CP is the most common and costly form of chronic motor disability in children, with a prevalence of 2 to 4 per 1,000 live births in the United States (US), and the condition is more common in boys than in girls. Although there have been no general studies of life expectancy in people with CP, most children affected by CP live between 30 and 70 years, depending on the severity of the condition. In general, a child with a mild case of CP usually lives longer than a child with mobility and intellectual limitations. In the US, there are about 764,000 children and adults with CP, including about 500,000 children under the age of 18 years. Prematurity is the most common cause of CP, but other causes include stroke, hypoxic ischemic injury, infection, or brain malformation.

Complications of CP may include eye movement abnormalities, communication problems, swallowing difficulty, poor weight gain, social isolation, hip dysplasia and dislocation, scoliosis, osteopenia and fractures, and pain. A variety of movement disorders are associated with CP, including spasticity, dyskinesia (dystonia, chorea, athetosis, and even ballismus), and ataxia. Many patients with CP present with mixed types of movement disorders.

Dyskinesia is believed to result from an insult of nonprogressive nature in the basal ganglia of the brain. Dyskinesia in cerebral palsy (DCP) is a hyperkinetic movement disorder characterized by abnormal involuntary movements of the dystonic and choreiform types in approximately 6% to 15% of patients with CP. DCP is a rare disease, and based on the above prevalence numbers of CP in the US, one could assume that approximately 30,000 to 75,000 children <18 years of age and 16,000 to 40,000 adults have DCP.

There are currently no approved treatments for DCP, which is a serious disease with an unmet medical need. Current treatment options (off-label use) to treat dystonia and chorea include tetrabenazine, dopaminergic, or gamma-aminobutyric acidergic interventions, but these show high variability in response. Botulinum neurotoxin A is also in clinical use for the treatment of spasticity and dystonia and is considered modestly effective in selected patients, but it does not meet the full treatment need. Naxibimols, a non-smoked cannabis derivative, was approved to treat spasticity associated with multiple sclerosis in the United Kingdom in 2010 and is being investigated to treat spasticity in CP. Currently, there are very few agents with novel mechanisms of action in development for movement disorders in CP. Dalfampridine, a small-molecule potassium channel blocker thought to restore conduction in central demyelinated axons, is approved for use in multiple sclerosis but has failed to demonstrate functional improvement in patients with CP.

Thus, a need exists for effective treatments for DCP.

SUMMARY

The present disclosure is directed to methods of treating dyskinesia in cerebral palsy in a human patient comprising administering to the patient a therapeutically effective amount of a compound having the Formula (I) or Formula (II) or a combination thereof:

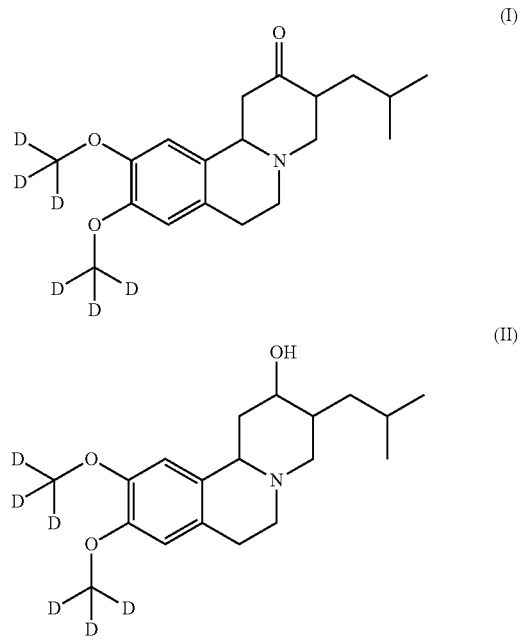

or pharmaceutically acceptable salt thereof, wherein each position represented as D has deuterium enrichment of no less than about 10%.

The present disclosure also is directed to methods of treating dyskinesia in cerebral palsy in a human patient, comprising administering an daily amount of deutetrabenazine of about 6 mg/day to about 48 mg/day, in one or two doses, to the patient, wherein the patient's abnormal involuntary movements associated with dyskinesia in cerebral palsy are reduced relative to the patient's abnormal involuntary movements associated with dyskinesia in cerebral palsy at baseline.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a", "an", and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "composition", "composition of compounds", "compound", "drug", "pharmacologically active agent", "active agent", "therapeutic", "therapy", "treatment", or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative, or palliative treatment. As used herein, the term "treating" includes alleviating or reducing at least one adverse or negative effect or symptom of a condition, disease or disorder. This condition, disease or disorder refers to DCP.

The term "administering" means either directly administering a compound or composition of the present invention, or administering a prodrug, derivative or analog which will form an equivalent amount of the active compound or substance within the body.

The terms "subject", "individual", and "patient" are used interchangeably herein, and refer to a human, to whom treatment, including prophylactic treatment, with the pharmaceutical composition according to the present invention, is provided.

"Pharmaceutically acceptable" refers to those compounds, materials, compositions, and/or dosage forms which are, within the scope of sound medical judgment, suitable for contact with the tissues of human beings without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These pharmaceutically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

The terms "point" and "score" are used interchangeably herein, and refer to the measure of a certain rating scale.

In some aspects, the present disclosure is directed to methods of treating DCP in a human patient comprising administering to the patient a therapeutically effective amount of a compound of Formula (I) or Formula (II) or a combination thereof:

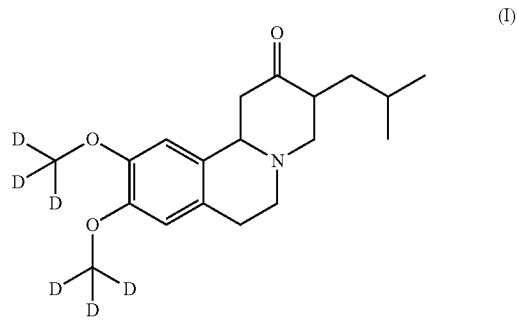 [SMILES: [2H]C([2H])([2H])Oc1cc2c(cc1OC([2H])([2H])[2H])C1CC(=O)C(CC(C)C)CN1CC2]

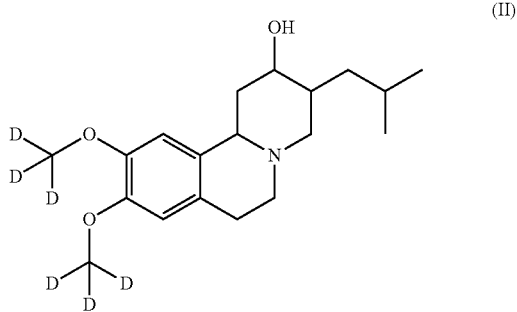 [SMILES: [2H]C([2H])([2H])Oc1cc2c(cc1OC([2H])([2H])[2H])C1CC(O)C(CC(C)C)CN1CC2]

or pharmaceutically acceptable salt thereof, wherein each position represented as D has deuterium enrichment of no less than about 10%.

In some embodiments the method comprised administration of the compound of Formula (I). The compound of Formula (I), which has the chemical name 1,3,4,6,7,11b-hexahydro-9,10-di(methoxy-d3)-3-(2-methylpropyl)-2H-benzo[a]quinolizin-2-one, has two stereogenic carbon atoms, which give rise to four stereo isomers of the compound of Formula (I): IA, IB, IC, ID:

As used herein, the compound of Formula (I) refers to compounds of Formulae IA, IB, IC, or ID, as well as mixtures of compounds of Formulae IA, IB, IC, or ID in any proportion.

In some embodiments, the compound of Formula (I) refers to deutetrabenazine.

In some embodiments the method comprises administration of the compound of Formula (II). The compound of Formula (II), which has the chemical name 3-isobutyl-9,10-bis(methoxy-d3)-1,3,4,6,7,11b-hexahydro-2H-pyrido[2,1-a]isoquinolin-2-ol, has three stereogenic carbon atoms, which give rise to eight stereoisomers of the compound of Formula (II): IIA, IIB, IIC, IID, IIE, IIF, IIG, IIH:

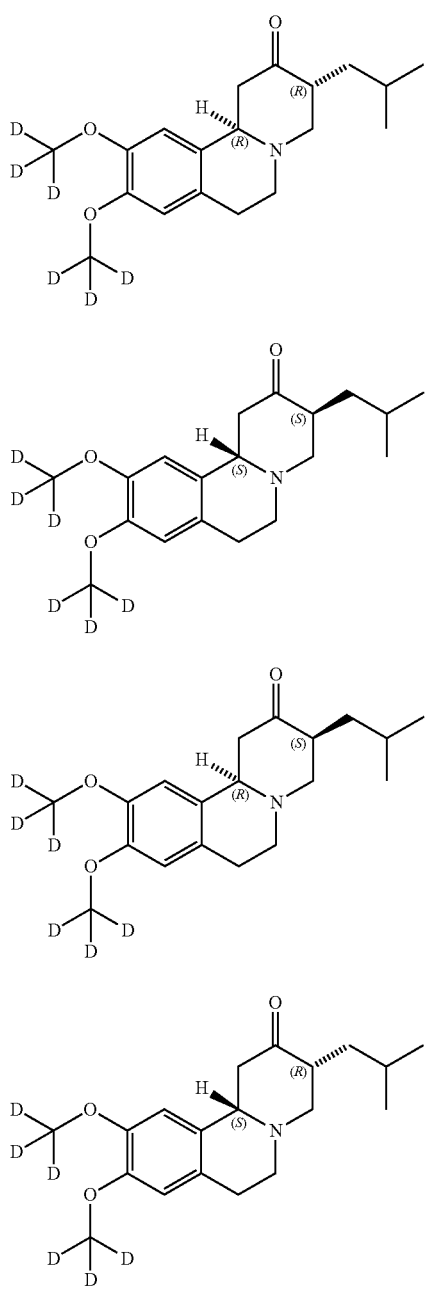

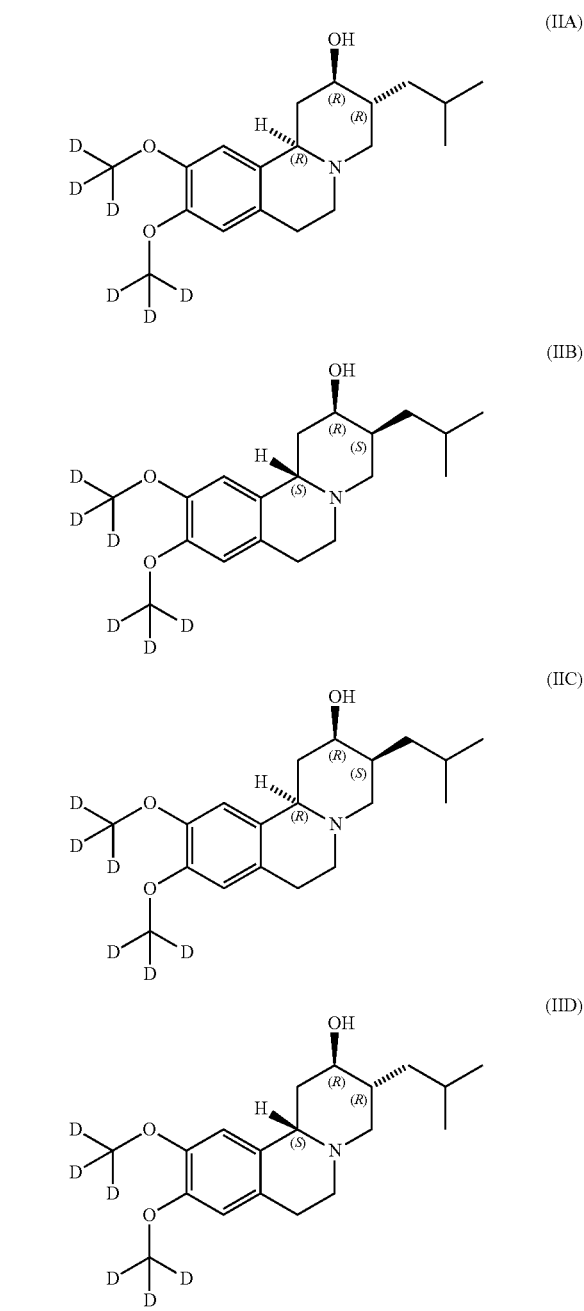

A racemic mixture of the (R,R) and (S,S) stereoisomers (i.e., a mixture of IA and IB) is referred to as deutetrabenazine. In some embodiments the method comprises administration of the racemic mixture of the (R,R) and (S,S) stereoisomers (i.e., a mixture of IA and IB) referred to as deutetrabenazine.

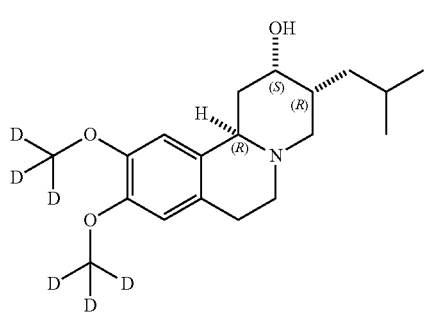
(IIE)

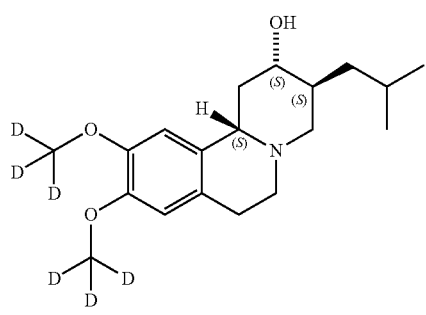
(IIF)

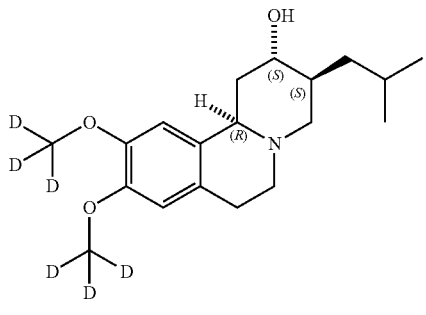
(IIG)

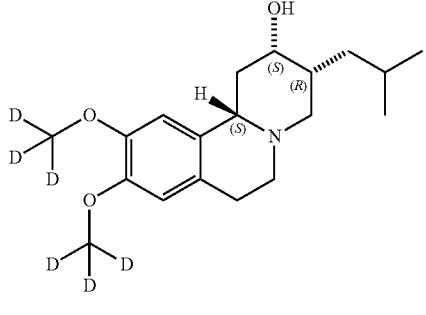
(IIH)

As used herein, the compound of Formula (II) refers to compounds of Formulae IIA, IIB, IIC, IID, IIE, IIF, IIG, IIH as well as mixtures of compounds of Formula IIA, IIB, IIC, IID, IIE, IIF, IIG, or IIH in any proportion.

Deutetrabenazine is metabolically reduced to deuterated alpha-dihydrotetrabenazine (α-HTBZ) (i.e., IIA and IIF) and deuterated beta-dihydrotetrabenazine (β-HTBZ) (i.e., IIB and IIE).

In some aspects, the method of the disclosure comprises administering a compound of Formula (I) or Formula (II) or a combination thereof, or a pharmaceutically acceptable salt thereof, wherein each position represented as D has deuterium enrichment of no less than about 10%. As used herein, deuterium enrichment refers to the percentage of hydrogen atoms at a given position that are the deuterium isotope (i.e., $^2H$) rather than either the $^1H$ and/or $^3H$ isotopes. For example, a deuterium enrichment of 10% means that 10% of the hydrogen atoms at a given position are deuterium, and 90% of the hydrogen atoms at that position are the $^1H$ and/or $^3H$ isotopes. Methods of determining the hydrogen isotope content are known to those of skill the art and include mass spectroscopy and NMR.

In some embodiments of the methods of the disclosure, each position in Formula (I) or Formula (II) represented as D has deuterium enrichment of no less than about 10%.

In other embodiments of the methods of the disclosure, each position in Formula (I) or Formula (II) represented as D has deuterium enrichment of no less than about 20%.

In other embodiments of the methods of the disclosure, each position in Formula (I) or Formula (II) represented as D has deuterium enrichment of no less than about 50%.

In other embodiments of the methods of the disclosure, each position in Formula (I) or Formula (II) represented as D has deuterium enrichment of no less than about 70%.

In other embodiments of the methods of the disclosure, each position in Formula (I) or Formula (II) represented as D has deuterium enrichment of no less than about 80%.

In other embodiments of the methods of the disclosure, each position in Formula (I) or Formula (II) represented as D has deuterium enrichment of no less than about 90%.

In other embodiments of the methods of the disclosure, each position in Formula (I) or Formula (II) represented as D has deuterium enrichment of no less than about 98%.

In some aspects, in the methods of the disclosure, administration of Formula (I) results in a substantially increased maximum tolerated dose, decreased toxicity, an increased half-life ($t_{1/2}$), or lowered maximum plasma concentration (Cmax) of the minimum efficacious dose (MED), or a combination thereof, as compared to an equally efficacious dose of the corresponding non-deuterated compound.

As used herein, the corresponding non-deuterated compound of Formula (I) refers to a compound having the structure

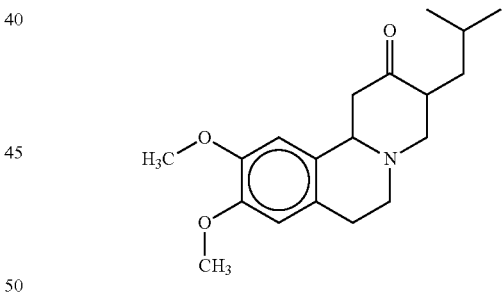

The corresponding non-deuterated compound of Formula (II) refers to a compound having the structure

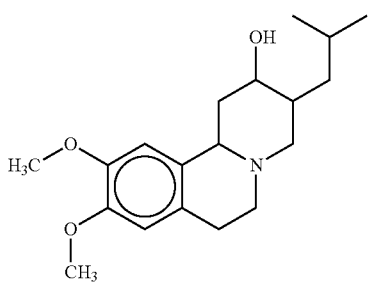

As used herein, with respect to the compound of Formula (I), an equally efficacious dose of the corresponding non-deuterated compound refers to a dose of the corresponding non-deuterated compound that produces the same improvement in the patient's dyskinesia in cerebral palsy as a specific dose of the compound of Formula (I). With respect to the compound of Formula (II), an equally efficacious dose of the corresponding non-deuterated compound refers to a dose of the corresponding non-deuterated compound that produces the same improvement in the patient's dyskinesia in cerebral palsy as a specific dose of the compound of Formula (II).

In some aspects, administration of the compound of Formula (I), (II), or combination thereof results in a substantially increased maximum tolerated dose as compared to administration of an equally efficacious dose of the corresponding non-deuterated compound.

In other aspects, administration of the compound of Formula (I), (II), or combination thereof results in a lower toxicity as compared to administration of an equally efficacious dose of the corresponding non-deuterated compound.

In other aspects, administration of the compound of Formula (I), (II), or combination thereof results in an increased half-life ($t_{1/2}$) of the compound of Formula (I) or (II), as compared to an equally efficacious dose of the corresponding non-deuterated compound.

In other aspects, administration of the compound of Formula (I), (II), or combination thereof results in a lowered Cmax of the MED as compared to administration an equally efficacious dose of the corresponding non-deuterated compound.

In some aspects, the methods of the disclosure are directed to treating dyskinesia in cerebral palsy (DCP) in a human patient. "Dyskinesia in cerebral palsy" refers to a hyperkinetic movement disorder characterized by abnormal involuntary movements of the dystonic and/or choreiform types. Dystonic abnormal involuntary movements result from involuntary muscle spasms. Choreiform types of abnormal involuntary movements include chorea, athetosis, and ballism/ballismus.

In some embodiments of the methods of the disclosure, the abnormal involuntary movements associated with DCP are of dystonic type.

In other embodiments of the methods of the disclosure, the abnormal involuntary movements associated with DCP are of choreiform type.

In other embodiments of the methods of the disclosure, the abnormal involuntary movements associated with DCP are of dystonic type and choreiform type.

In yet other embodiments of the methods of the disclosure, the abnormal involuntary movements associated with DCP are of dystonic type or choreiform type.

In some aspects, the methods of the disclosure are performed on a human patient. In some embodiments of the methods of the disclosure, the human patient is a pediatric patient. As used herein, a "pediatric patient" refers to a patient who is 18 years of age or younger. In some embodiments of the methods of the disclosure, the human patient is an adult patient. As used herein, an "adult patient" refers to a patient who is older than 18 years of age.

In some embodiments of the methods of the disclosure, the patient is between 6 and 18 years of age.

In other embodiments of the methods of the disclosure, the patient is between 6 to <12 years of age.

In other embodiments of the methods of the disclosure, the patient is between 12 and 18 years of age.

In yet other embodiments of the methods of the disclosure, the patient is younger than 6 years of age.

In some aspects of the methods of the disclosure the patent is about 1, 2, 3, 4, 5, 6, 7, 8, 9, 10, 11, 12, 13, 14, 15, 16, 17 or about 18 years old. In some aspects of the methods of the disclosure, the patient is about 1, 2, 3, 4, are about 5, years old. In some aspects of the methods of the disclosure, the patient is about 6, 7, 8, 9, 10, or about 11 years old. In some aspects of the methods of the disclosure the patient is about 12, 13, 14, 15, 16, 17 or about 18 years of age.

In some aspects, in the methods of the disclosure the patient is further administered an additional therapeutic agent. As used herein, an additional therapeutic agent refers to an agent other than the compound of Formula (I) and/or Formula (II) that is administered to treat an aspect of the patient's cerebral palsy, such as, for example, eye movement abnormalities, communication problems, swallowing difficulty, poor weight gain, social isolation, hip dysplasia and dislocation, scoliosis, osteopenia and fractures, pain, and movement disorders. Exemplary additional therapeutic agents include anticholinergics (e.g., benztropine mesylate, carbidopa-levodopa, glycopyrrolate, procyclidine hydrochloride, and trihexyphenidyl hydrochloride), anticonvulsants (e.g., gabapentin, lamotrigine, oxcarbazepine, topiramate, and zonisamide), antidepressants (e.g., citalopram, escitalopram, fluoxetine, paroxetine, and sertraline), antispastic (e.g., botulinum toxin, diazepam, dantrolene, cyclobenzadrine, intrathecal baclofen, and tizanidine), and anti-inflammatories (e.g., aspirin, corticosteroids, nonsteroidal anti-inflammatory drugs (NSAIDs), and steroids). In some embodiments of the method the administration of the additional therapeutic agent in concomitant with, prior to, or following the administration of the compound of Formula (I), Formula (II) or a combination thereof.

In some aspects, the disclosure is directed to methods of treating dyskinesia in cerebral palsy in a human patient, comprising administering to the patient a daily amount of a compound of Formula (I) of about 6 mg/day to about 48 mg/day, in one or two doses.

In some aspects of the methods of the disclosure, the patient is administered a daily amount of deutetrabenazine of about 6 mg/day to about 48 mg/day, in one or two doses.

As used herein, the terms "daily amount" or "daily dose" can be used interchangeably and refer to the dose to be administered per day shown to be optimal for example, by dose titration or other method determined by, for example, the attending physician. The period of time just prior to initiation of deutetrabenazine therapy is referred to as the "baseline". The patient's condition just prior to initiation of deutetrabenazine therapy can be referred to as the patient's baseline condition. The daily amount or daily dose is administered to the patient in one or two doses, further described herein below.

In some embodiments, the daily amount of deutetrabenazine is 6 mg/day to 48 mg/day. In some embodiments, the daily amount of deutetrabenazine is 6 mg/day.

In some embodiments, the daily amount of deutetrabenazine is 12 mg/day.

In some embodiments, the daily amount of deutetrabenazine is 18 mg/day.

In some embodiments, the daily amount of deutetrabenazine is 24 mg/day.

In some embodiments, the daily amount of deutetrabenazine is 30 mg/day.

In some embodiments, the daily amount of deutetrabenazine is 36 mg/day.

In some embodiments, the daily amount of deutetrabenazine is 42 mg/day.

In some embodiments, the daily amount of deutetrabenazine is 48 mg/day.

In some aspects of the methods of the disclosure, the daily amount can be administered in one or two doses. In some embodiments the daily amount is administered in a single dose. In other embodiments, the daily amount is administered in two doses.

When the daily dose is administered in two doses, the two doses can be equal amounts, or can be different amounts. In some embodiments, each of the two doses are of an equal amount.

When the daily amount is administered in two doses, the two doses can be equal amounts, or can be different amounts. In some embodiments, each of the two doses of the daily amount are equal doses.

When the daily amount is administered in two doses, an intervening time period separates the dose administrations. In some embodiments, the second dose is administered about 8 to 10 hours after the first dose. In other embodiments, the second dose is administered about 8 hours after the first dose. In other embodiments, the second dose is administered about 10 hours after the first dose.

In some embodiments, a titration regimen is used to determine an initial daily dose of the compound of Formula (I). In some embodiments, a titration regimen is used to determine an initial daily dose of the compound of Formula (II) or a combination of Formula (I) and Formula (II). In some embodiments, the initial daily dose is different from the maintenance daily dose.

In some embodiments, the administration comprises:
a) administering to the subject an initial daily amount of deutetrabenazine of at least about 6 mg per day;
b) determining after about one week the degree of control of abnormal involuntary movement associated with DCP achieved with the initial daily amount and the tolerability of the initial daily amount;
c) increasing the daily amount of the deutetrabenazine upward by 6 mg/day or more to a subsequent daily amount if the degree of control of abnormal involuntary movement associated with DCP is inadequate and the initial daily amount is tolerable;
d) optionally, repeating steps b) and c) until the degree of control of abnormal involuntary movement associated with DCP is adequate and the daily amount of the deutetrabenazine is tolerable; and
e) if any subsequent amount is not tolerated, decreasing the daily amount downward by 6 mg/day or more to a subsequent daily amount.

In some aspects, the treating results in maintaining the patient's abnormal involuntary movements associated with DCP, relative to the patient's abnormal involuntary movements associated with DCP at baseline. As used in this context, "maintaining the patient's abnormal involuntary movements" means that the patient's abnormal involuntary movements associated with DCP do not change relative to baseline. Thus, the patient's abnormal involuntary movements associated with DCP remain stabilized, they do not improve but do not worsen. Such treatment represents a clinical benefit to patients with a history of worsening abnormal involuntary movements associated with DCP.

In some aspects of the methods of the disclosure, the treatment with a compound of Formula (I) and/or a compound of Formula (II) results in a reduction in the patient's abnormal involuntary movements associated with DCP, relative to the patient's abnormal involuntary movements associated with DCP at baseline. In some aspects of the methods of the disclosure, the treatment with a compound of Formula (I) results in a reduction in the patient's abnormal involuntary movements associated with DCP, relative to the patient's abnormal involuntary movements associated with DCP at baseline. In some aspects of the methods of the disclosure, the treatment with deutetrabenazine results in a reduction in the patient's abnormal involuntary movements associated with DCP, relative to the patient's abnormal involuntary movements associated with DCP at baseline.

In some aspects of the methods of the disclosure, the treatment with a compound of Formula (II) results in a reduction in the patient's abnormal involuntary movements associated with DCP, relative to the patient's abnormal involuntary movements associated with DCP at baseline. In some aspects of the methods of the disclosure, the treatment with deuterated α-HTBZ or deuterated β-HTBZ results in a reduction in the patient's abnormal involuntary movements associated with DCP, relative to the patient's abnormal involuntary movements associated with DCP at baseline.

In some aspects, the patient's abnormal involuntary movements associated with DCP are measured using a clinical assessment instrument, such as, for example, at least one of the rating scales: a) the MD-CRS part II; b) the MD-CRS part I; c) the CaGI-I; and d) the CGI-I. One such clinical instrument is the Movement Disorder-Childhood Rating Scale Index (MD-CRS). See, e.g., Battini R, et al. Responsiveness of the MD-Childhood Rating Scale in dyskinetic cerebral palsy patients undergoing anticholinergic treatment. Eur J Paediatr Neurol 2014;18(6):698-703; Battini R, et al. Movement Disorder-Childhood Rating Scale: reliability and validity. Pediatr Neurol 2008;39(4):259-65, the entireties of which are incorporated by reference herein.

The MD-CRS has 2 parts, part I and part II, where the higher the score is indicative of a worsened condition.

The MD-CRS part I evaluates the impact of DCP on the activities of the patient and provides a general assessment of the movement disorder on motor function (7 items), oral/verbal function (3 items), self-care (3 items), and attention/alertness (2 items) on a scale of 0 (present) to 4 (absent). The total score of MD-CRS part I (0 to 60) can be normalized to a 0 to 1 range referred to as "Index I".

MD-CRS part II is a specific motor assessment of severity of the movement disorder, in this case, involuntary movements associated with DCP. MD-CRS part II evaluates the severity of the movement disorder in a scale of 0 to 4 in each of 7 body regions in which dyskinesia can be seen in patients with CP. The maximum possible total score on the MD-CRS part II is therefore 28. The total score of MD-CRS part II (0 to 28) can be normalized to a 0 to 1 range referred to as "Index II". In the MD-CRS part II, a score of 0 refers to absence of a movement disorder and a score of 4 refers to a situation where movement disorder is present during all of the tasks for the region examined and/or involves 3 or more of the other regions, making completion impossible. The 7 body regions evaluated with the MD-CRS part II are (i) eye and periorbital region, (ii) face, (iii) tongue and perioral region, (iv) neck, (v) trunk, (vi) upper limb, and (vii) lower limb. The MD-CRS does not differentiate between dyskinesia in cerebral palsy of the dystonic type or choreiform type, and the worst dyskinesia in any of the regions observed during the assessment session is taken as the score for each affected body region.

Another assessment instrument is the Caregiver Global Impression of Improvement Scale (CaGI-I). The CaGI-I is single item questionnaire to assess the caregiver's impression of improvement in dyskinesia in cerebral palsy symptoms after initiating therapy. The scale is a caregiver-reported outcome that aims to evaluate all aspects of the patient's health and determine whether there has been an overall improvement in dyskinesia symptoms. The caregiver ratings are 1=very much improved (since the initiation of treatment); 2=much improved; 3=minimally improved; 4=no change from baseline (symptoms remain essentially unchanged); 5=minimally worse; 6=much worse; or 7=very much worse (since the initiation of treatment).

Another assessment instrument is the Clinical Global Impression of Improvement (CGI-I, a clinician reported outcome that uses a 7-point scale that allows the clinician to compare the patient's condition since initiation of treatment to the baseline condition as follows: 1=very much improved since the initiation of treatment (nearly all better; good level of functioning; minimal symptoms; represents a very substantial change); 2=much improved (notably better with significant reduction of symptoms; increase in the level of functioning but some symptoms remain); 3=minimally improved (slightly better with little or no clinically meaningful reduction of symptoms; represents very little change in basic clinical status, level of care, or functional capacity); 4=no change from baseline (symptoms remain essentially unchanged); 5=minimally worse (slightly worse but may not be clinically meaningful; may represent very little change in basic clinical status or functional capacity); 6=much worse (clinically significant increase in symptoms and diminished functioning); 7=very much worse since the initiation of treatment (severe exacerbation of symptoms and loss of functioning). See, e.g., Busner J, Targum S D. The Clinical Global Impressions Scale: Applying a Research Tool in Clinical Practice. Psychiatry (Edgmont) 2007;4(7):28-37 the entirety of which is incorporated by reference herein.

Another assessment instrument is the Clinical Global Impression of Severity (CGI-S), which uses a 7-point Likert scale to assess dyskinesia severity as follows (with anchor points for choosing the most appropriate severity level caused by DCP): 1=normal (not at all ill, symptoms of disorder not present past 7 days); 2=borderline (subtle or suspected pathology); 3=mild (clearly established symptoms with minimal, if any, distress or difficulty in social and/or occupational function); 4=moderate (overt symptoms causing noticeable, but modest, functional impairment or distress; symptom level may warrant medication); 5=marked (intrusive symptoms that distinctly impair social/occupational function or cause intrusive levels of distress); 6=severe (disruptive symptoms, behavior and function are frequently influenced by symptoms, may require assistance from others); 7=extreme (symptoms drastically interferes in many life functions; may be hospitalized).

Another assessment instrument is the Pediatric Evaluation Disability Inventory-Computer Adapted Test (PEDI-CAT), which is a clinical assessment for children and youth. The PEDI-CAT comprises a comprehensive item bank of 276 functional activities acquired throughout infancy, childhood, and young adulthood. See, e.g., Dumas H M, Fragala-Pinkham M A. Concurrent Validity and Reliability of the Pediatric Evaluation of Disability Inventory-Computer Adaptive Test Mobility Domain. Pediatric Physical Therapy 2012;24:171-76, the entirety of which is incorporated by reference herein.

Another assessment instrument is the Pediatric Quality of Life Inventory (PedsQL), which is a health-related quality-of-life instrument that consists of a well-validated generic core measure and some condition and disease-specific modules (Varni, J W, et al. The PedsQL™ in pediatric cerebral palsy: Reliability, validity, and sensitivity of the Generic Core Scales and Cerebral Palsy Module. Developmental Medicine and Child Neurology 2006;48:442-49), the entirety of which is incorporated by reference herein. The 35-item PedsQL 3.0 CP module encompasses 7 scales: (1) Daily Activities (9 items); (2) School Activities (4 items); (3) Movement and Balance (5 items); (4) Pain and Hurt (4 items); (5) Fatigue (4 items); (6) Eating Activities (5 items); and (7) Speech and Communication (4 items). The instructions ask how much of a problem each item has been during the past 1 month. A 5-point response scale is utilized across child self-report and parent proxy report as follows: 0=never a problem; 1=almost never a problem; 2=sometimes a problem; 3=often a problem; 4=almost always a problem.

Another assessment instrument is the Patient Global Impression of Improvement (PGI-I), which is a single item questionnaire to assess the patient's impression of improvement in dyskinesia symptoms after initiating the disclosed therapy. PGI-I is a patient-reported outcome that aims to evaluate all aspects of a patient's health and determine whether or not there has been an overall improvement in dyskinesia symptoms. The patient has to select the 1 response from the visual response options ("emojis") that gives the most accurate description of his/her state of health and overall status: 1=much improved (since the initiation of treatment); 2=somewhat improved; 3=no change; 4=somewhat worse; 5=much worse (since the initiation of treatment).

Another assessment instrument is the Unified Huntington's Disease Rating Scale-Total Motor Score (UHDRS-TMS), comprises 15 items and assesses eye movements, speech, alternating hand movements, dystonia, chorea, and gait. The UHDRS-TMS is calculated as the sum of the 31 motor assessments, each of which ranges between 0 to 4 points. The total minimum score is 0 (absent) and the maximum score is 124 (worst). The Unified Huntington's Disease Rating Scale-Total Maximal Chorea (UHDRS-TMC) is part of the UHDRS-TMS assessment and assesses the severity of chorea in the face, mouth, trunk, and the 4 extremities. The minimum score is 0 (absent) and the maximum score is 28 (marked/prolonged). The Unified Huntington's Disease Rating Scale-Total Maximal Dystonia (UHDRS-TMD) is part of the UHDRS-TMS assessment and assesses the severity of dystonia in the trunk and the 4 extremities. The minimum score is 0 (absent) and the maximum score is 20 (marked/prolonged) See, e.g., Huntington Study Group. Unified Huntington's Disease Rating Scale: reliability and consistency. Huntington Study Group. Mov Disord 1996;11(2):136-42, the entirety of which is incorporated by reference herein.

Another assessment instrument is the Canadian Occupational Performance Measure (COPM). The COPM has been designed to assess patient outcomes in the areas of self-care, productivity and leisure. Using a semi-structured interview, the COPM is a 5-step process which measures individual, patient-identified problem areas in daily function. Two scores, for performance and satisfaction with performance, are obtained. Law M, et al. The Canadian occupational performance measure: an outcome measure for occupational therapy. Can J Occup Ther 1990 April;57(2):82-7, the entirety of which is incorporated by reference herein.

In some aspects, the safety of the treatment is measured by the Columbia-Suicide Severity Rating Scale (C-SSRS), which measures the frequency and severity of suicidal ideation or behavior. See, e.g., Posner K, et al. The Columbia-Suicide Severity Rating Scale: Initial Validity and Internal Consistency Findings From Three Multisite Studies With Adolescents and Adults. American Journal of Psychiatry 2011;168(12):1266-77, the entirety of which is incorporated by reference herein.

In some embodiments of the methods of the disclosure, the patient's abnormal involuntary movements associated with DCP are measured by at least one clinical assessment instrument For example, in some aspects of the methods of the disclosure, the patient's abnormal involuntary movements associated with DCP are measured by at least one of Movement Disorder-Childhood Rating Scale Index (MD-CRS);
Caregiver Global Impression of Improvement Scale (CaGI-I);
Clinical Global Impression of Improvement (CGI-I);
Clinical Global Impression of Severity (CGI-S);
Pediatric Evaluation Disability Inventory-Computer Adapted Test (PEDI-CAT);
Pediatric Quality of Life Inventory (PedsQL);
Patient Global Impression of Improvement (PGI-I);
Unified Huntington's Disease Rating Scale-Total Motor Score (UHDRS-TMS);
Columbia-Suicide Severity Rating Scale (C-SSRS)
Canadian Occupational Performance Measure (COPM).

In some embodiments of the methods of the disclosure, the patient's abnormal involuntary movements associated with DCP are measured by at least one of: a) the MD-CRS part II; b) the MD-CRS part I; c) the CaGI-I; and d) the CGI-I.

In some embodiments, the reduction in abnormal involuntary movements associated with DCP is demonstrated by at least one of:
a) a reduction in the MD-CRS part II total score from baseline to week 15;
b) a reduction in the MD-CRS part I total score from baseline to week 15;
c) a reduction in the CaGI-I score from baseline to week 15; and
d) a reduction in the CGI-I score from baseline to week 15.

In some embodiments of the methods of the disclosure, the patient's abnormal involuntary movements associated with DCP are measured by a change from baseline to week 15 in the MD-CRS part II score.

In some embodiments of the methods of the disclosure, the patient has a total score of ≥8 on the MD-CRS part II items at baseline.

In some embodiments of the methods of the disclosure, the patient has a total score of ≥10 on the MD-CRS part II items at baseline.

In some embodiments of the methods of the disclosure, the patient has a total score of ≥12 on the MD-CRS part II items at baseline.

In some embodiments of the methods of the disclosure, the patient has a total score of ≥14 on the MD-CRS part II items at baseline.

In some embodiments of the methods of the disclosure, the patient has a total score of ≥16 on the MD-CRS part II items at baseline.

In some embodiments of the methods of the disclosure, the patient has a total score of ≥18 on the MD-CRS part II items at baseline.

In some embodiments of the methods of the disclosure, the patient has a total score of ≥20 on the MD-CRS part II items at baseline.

In some embodiments of the methods of the disclosure, the patient's abnormal involuntary movements associated with DCP are measured by a change from baseline to week 15 in the MD-CRS part I score.

In some embodiments of the methods of the disclosure, the patient's MD-CRS part I total score is reduced by about 1-8 points relative to baseline. In some embodiments of the methods of the disclosure, the patient's MD-CRS part I total score is reduced by about 2-4 points relative to baseline. In some embodiments, the patient's MD-CRS part I total score is reduced by at least 1 point relative to baseline. In some embodiments, the patient's MD-CRS part I total score is reduced by at least 2 points relative to baseline. In some embodiments, the patient's MD-CRS part I total score is reduced by at least 3 points relative to baseline. In some embodiments, the patient's MD-CRS part I total score is reduced by at least 4 points relative to baseline. In some embodiments, the patient's MD-CRS part I total score is reduced by at least 5 points relative to baseline. In some embodiments, the patient's MD-CRS part I total score is reduced by at least 6 points relative to baseline. In some embodiments, the patient's MD-CRS part I total score is reduced by at least 7 points relative to baseline. In some embodiments, the patient's MD-CRS part I total score is reduced by at least 8 points relative to baseline. In some embodiments of the methods of the disclosure, the reductions in the MD-CRS part I total score disclosed herein are observed at 15 weeks from start of treatment. In some embodiments of the methods of the disclosure, the reduction in the MD-CRS part I total score disclosed herein is observed for at least 15 weeks from start of treatment In some embodiments of the methods of the disclosure, the patient's abnormal involuntary movements are measured by a change from baseline to week 15 in the CaGI-I rating Scale.

In some embodiments of the methods of the disclosure, the patient's CaGI-I score is reduced by about 0.2-0.8 points relative to baseline. In some embodiments of the methods of the disclosure, the patient's CaGI-I score is reduced by about 0.5-0.7 points relative to baseline. In some embodiments of the methods of the disclosure, the patient's CaGI-I score is reduced by at least 0.2 points relative to baseline. In some embodiments of the methods of the disclosure, the patient's CaGI-I score is reduced by at least 0.3 points relative to baseline. In some embodiments of the methods of the disclosure, the patient's CaGI-I score is reduced by at least 0.4 points relative to baseline. In some embodiments of the methods of the disclosure, the patient's CaGI-I score is reduced by at least 0.5 points relative to baseline. In some embodiments of the methods of the disclosure, the patient's CaGI-I score is reduced by at least 0.6 points relative to baseline. In some embodiments of the methods of the disclosure, the patient's CaGI-I score is reduced by at least 0.7 points relative to baseline. In some embodiments of the methods of the disclosure, the reductions in the CaGI-I score disclosed herein are observed at 15 weeks from start of treatment. In some embodiments of the methods of the disclosure, the reduction in the CaGI-I score disclosed herein is observed for at least 15 weeks from start of treatment.

In some embodiments of the methods of the disclosure, the patient's abnormal involuntary movements are measured by a change from baseline to week 15 in the CGI-I rating Scale.

In some embodiments of the methods of the disclosure, the patient's CGI-I score is reduced by about 0.2-0.8 points relative to baseline. In some embodiments of the disclosure, the patient's CGI-I score is reduced by about 0.5-0.7 points relative to baseline. In some embodiments of the methods of the disclosure, the patient's CGI-I score is reduced by at least 0.2 points relative to baseline. In some embodiments of the methods of the disclosure, the patient's CGI-I score is reduced by at least 0.3 points relative to baseline. In some embodiments of the methods of the disclosure, the patient's CGI-I score is reduced by at least 0.4 points relative to baseline. In some embodiments of the methods of the disclosure, the patient's CGI-I score is reduced by at least 0.5 points relative to baseline. In some embodiments of the methods of the disclosure, the patient's CGI-I score is reduced by at least 0.6 points relative to baseline. In some embodiments of the methods of the disclosure, the patient's CGI-I score is reduced by at least 0.7 points relative to baseline. In some embodiments of the methods of the disclosure, the reductions in the CGI-I score disclosed herein are observed at 15 weeks from start of treatment. In some embodiments of the methods of the disclosure, the reduction in the CGI-I score disclosed herein is observed for at least 15 weeks from start of treatment.

In some aspects of the methods of the disclosure, the severity of the patient's abnormal involuntary movements associated with DCP is reduced relative to the severity of the patient's abnormal involuntary movements at baseline.

In some aspects, the reduction in the severity of the patient's abnormal involuntary movements associated with DCP is measured using the MD-CRS part II.

In some embodiments of the methods of the disclosure, the patient's MD-CRS part II total score is reduced by about 0.5-10 points relative to baseline. In some embodiments of the methods of the disclosure, the patient's MD-CRS part II total score is reduced by about 0.5-4 points relative to baseline. In some embodiments, the patient's MD-CRS part II total score is reduced by at least 0.5 point compared to the patient's MD-CRS part II total score at baseline. In some embodiments, the patient's MD-CRS part II total score is reduced by at least 1 point compared to the patient's MD-CRS part II total score at baseline. In other embodiments, the patient's MD-CRS part II total score is reduced by at least 2 points compared to the patient's MD-CRS part II total score at baseline. In other embodiments, the patient's MD-CRS part II total score is reduced by at least 3 points compared to the patient's MD-CRS part II total score at baseline. In other embodiments, the patient's MD-CRS part II total score is reduced by at least 4 points compared to the patient's MD-CRS part II total score at baseline. In other embodiments, the patient's MD-CRS part II total score is reduced by at least 5 points compared to the patient's MD-CRS part II total score at baseline. In other embodiments, the patient's MD-CRS part II total score is reduced by at least 6 points compared to the patient's MD-CRS part II total score at baseline. In other embodiments, the patient's MD-CRS part II total score is reduced by at least 7 points compared to the patient's MD-CRS part II total score at baseline. In other embodiments, the patient's MD-CRS part II total score is reduced by at least 8 points compared to the patient's MD-CRS part II total score at baseline. In other embodiments, the patient's MD-CRS part II total score is reduced by at least 9 points compared to the patient's MD-CRS part II total score at baseline. In other embodiments, the patient's MD-CRS part II total score is reduced by at least 10 points compared to the patient's MD-CRS part II total score at baseline. In some embodiments of the methods of the disclosure, the reductions in the MD-CRS part II total score disclosed herein are observed at 15 weeks from start of treatment. In some embodiments of the methods of the disclosure, the reduction in the MD-CRS part II total score disclosed herein is observed for at least 15 weeks from start of treatment.

In some aspects of the methods of the disclosure, the patient's motor function is improved relative to the patient's motor function at baseline following administration of deutetrabenazine. In some embodiments, improvement of the patient's motor function is demonstrated in one or more of the seven body regions assessed by the MD-CRS part II: (i) eye and periorbital region, (ii) face, (iii) tongue and perioral region, (iv) neck, (v) trunk, (vi) upper limb, and (vii) lower limb, or combination thereof.

In some embodiments, the patient's motor function in the eye and periorbital region is improved relative to the patient's motor function at baseline following administration of deutetrabenazine. In some embodiments, the patient's motor function in the eye and periorbital region is improved relative to the patient's motor function at baseline following administration of deutetrabenazine as demonstrated by reduction in the eye and periorbital region score of the MD-CRS part II relative to the score at baseline.

In some embodiments, the patient's motor function in the face is improved relative to the patient's motor function at baseline following administration of deutetrabenazine. In some embodiments, the patient's motor function in the face is improved relative to the patient's motor function at baseline following administration of deutetrabenazine as demonstrated by reduction in the face score of the MD-CRS part II relative to the score at baseline.

In some embodiments, the patient's motor function in the tongue and perioral region is improved relative to the patient's motor function at baseline following administration of deutetrabenazine. In some embodiments, the patient's motor function in the tongue and perioral region is improved relative to the patient's motor function at baseline following administration of deutetrabenazine as demonstrated by reduction in the tongue and perioral region score of the MD-CRS part II relative to the score at baseline.

In some embodiments, the patient's motor function in the neck is improved relative to the patient's motor function at baseline following administration of deutetrabenazine. In some embodiments, the patient's motor function in the neck is improved relative to the patient's motor function at baseline following administration of deutetrabenazine as demonstrated by reduction in the neck score of the MD-CRS part II relative to the score at baseline.

In some embodiments, the patient's motor function in the trunk is improved relative to the patient's motor function at baseline following administration of deutetrabenazine. In some embodiments, the patient's motor function in the trunk is improved relative to the patient's motor function at baseline following administration of deutetrabenazine as demonstrated by reduction in the trunk score of the MD-CRS part II relative to the score at baseline.

In some embodiments, the patient's motor function in the trunk is improved relative to the patient's motor function at baseline following administration of deutetrabenazine. In some embodiments, the patient's motor function in the upper limbs is improved relative to the patient's motor function at baseline following administration of deutetrabenazine as demonstrated by reduction in the upper limbs score of the MD-CRS part II relative to the score at baseline.

In some embodiments, the patient's motor function in the lower limbs is improved relative to the patient's motor function at baseline following administration of deutetrabenazine. In some embodiments, the patient's motor function in the lower limbs is improved relative to the patient's motor function at baseline following administration of deutetrabenazine as demonstrated by reduction in the lower limbs score of the MD-CRS part II relative to the score at baseline.

In some aspects of the methods of the disclosure, the patient's oral/verbal function is improved relative to the patient's oral/verbal function at baseline following administration of deutetrabenazine. In some embodiments, the patient's oral/verbal function is improved relative to the patient's oral/verbal function at baseline following administration of deutetrabenazine as demonstrated by reduction in the oral/verbal function score on the MD-CRS part I. In some embodiments, the patient's oral/verbal score on the MD-CRS part I is reduced by 0.5 points or more from baseline. In some embodiments, the patient's oral/verbal score on the MD-CRS part I is reduced by 1 points or more from baseline. In some embodiments, the patient's oral/verbal score on the MD-CRS part I is reduced by 2 points or more from baseline. In some embodiments, the patient's oral/verbal score on the MD-CRS part I is reduced by 3 points or more from baseline. In some embodiments, the patient's oral/verbal score on the MD-CRS part I is reduced by 4 points from baseline.

In some aspects of the methods of the disclosure, the patient's self-care function is improved relative to the patient's self-care function at baseline following administration of deutetrabenazine. In some embodiments, the patient's self-care function is improved relative to the patient's self-care function at baseline following administration of deutetrabenazine as demonstrated by reduction in the self-care score on the MD-CRS part I. In some embodiments, the patient's self-care score on the MD-CRS part I is reduced by 0.5 points or more from baseline. In some embodiments, the patient's self-care score on the MD-CRS part I is reduced by 1 points or more from baseline. In some embodiments, the patient's self-care score on the MD-CRS part I is reduced by 2 points or more from baseline. In some embodiments, the patient's self-care score on the MD-CRS part I is reduced by 3 points or more from baseline. In some embodiments, the patient's self-care score on the MD-CRS part I is reduced by 4 points from baseline.

In some aspects of the methods of the disclosure, the patient's attention/alertness is improved relative to the patient's attention/alertness at baseline following administration of deutetrabenazine. In some embodiments, the patient's attention/alertness is improved relative to the patient's attention/alertness at baseline following administration of deutetrabenazine as demonstrated by reduction in the attention/alertness score on the MD-CRS part I. In some embodiments, the patient's attention/alertness score on the MD-CRS part I is reduced by 0.5 points or more from baseline. In some embodiments, the patient's attention/alertness score on the MD-CRS part I is reduced by 1 points or more from baseline. In some embodiments, the patient's attention/alertness score on the MD-CRS part I is reduced by 2 points or more from baseline. In some embodiments, the patient's attention/alertness score on the MD-CRS part I is reduced by 3 points or more from baseline. In some embodiments, the patient's attention/alertness score on the MD-CRS part I is reduced by 4 points from baseline.

In some aspects of the methods of the disclosure, the patient's abnormal involuntary movements have much or very much improved relative to baseline. In some embodiments, the improvement in the patient's abnormal involuntary movements is demonstrated by a score of 1 or 2 on the Caregiver Global Impression of Improvement Scale (CaGI-I) or a score of 1 or 2 on the Clinical Global Impression of Improvement (CGI-I).

In some embodiments of the methods of the disclosure, the patient's abnormal involuntary movements have much improved relative to baseline as demonstrated by a score of 2 on the CaGI-I.

In other embodiments of the methods of the disclosure, the patient's abnormal involuntary movements have much improved relative to baseline as demonstrated by a score of 2 on the CGI-I.

In some embodiments of the methods of the disclosure, the patient's abnormal involuntary movements have very much improved relative to baseline as demonstrated by a score of 1 on the CaGI-I.

In other embodiments of the methods of the disclosure, the patient's abnormal involuntary movements have very much improved relative to baseline as demonstrated by a score of 1 on the CGI-I.

In some aspects of the methods of the disclosure, the patient has a score of 4 or greater in the Clinical Global Impression of Severity (CGI-S) rating scale at baseline. The CGI-S measures dyskinesia severity using a 7-point scale: 1=normal (not at all ill, symptoms of disorder not present past 7 days); 2=borderline (subtle or suspected pathology); 3=mild (clearly established symptoms with minimal, if any, distress or difficulty in social and/or occupational function); 4=moderate (overt symptoms causing noticeable, but modest, functional impairment or distress; symptom level may warrant medication); 5=marked (intrusive symptoms that distinctly impair social/occupational function or cause intrusive levels of distress); 6=severe (disruptive symptoms, behavior and function are frequently influenced by symptoms, may require assistance from others); 7=extreme (symptoms drastically interferes in many life functions; may be hospitalized).

In some aspects of the methods of the disclosure, the patient's abnormal involuntary movements associated with DCP are reduced by at least 20% relative to baseline. In some embodiments, the percentage reduction is equivalent to the percentage change in the score on one of the clinical assessment instruments described herein.

In some aspects, the patient's on whom the methods of the present disclosure are performed weigh at least 12 kg at baseline. In some aspects, the dose of compound (e.g. Formula (I) or Formula (II)) administered to the patient depends on the patient's weight, and on whether the patient has a CYP2D6 impairment. As used herein, a CYP2D6 impairment means that the patient is administered a strong CYP2D6 inhibitor concurrently with the deutetrabenazine, or that the patient is a poor CYP2D6 metabolizer. Examples of strong CYP2D6 inhibitors include bupropion, fluoxetine, and paroxetine.

In some embodiments of the methods of the disclosure, the patient weighs 12 kg to <17 kg, for example, 12, 13, 14, 15, or about 16 kg, and the patient is administered a daily amount of deutetrabenazine of less than or equal to about 24 mg if the patient does not have a CYP2D6 impairment; or the patient is administered a daily amount of deutetrabenazine of less than or equal to about 12 mg if the patient has a CYP2D6 impairment.

In some embodiments of the methods of the disclosure, the patient weighs 17 kg to <30 kg, for example, 17, 18, 19, 20, 21, 22, 23, 24, 25, 26, 27, 28 or about 29 kg, and the patient is administered a daily amount of deutetrabenazine of less than or equal to about 30 mg if the patient does not have a CYP2D6 impairment; or the patient is administered a daily amount of deutetrabenazine of less than or equal to about 18 mg if the patient has a CYP2D6 impairment.

In some embodiments of the methods of the disclosure, the patient weighs 30 kg to <40 kg, for example, 30, 31, 32, 33, 34, 35, 36, 37, 38, or about 39 kg, and the patient is administered a daily amount of deutetrabenazine of less than or equal to about 42 mg if the patient does not have a CYP2D6 impairment; or the patient is administered a daily amount of deutetrabenazine of less than or equal to about 24 mg if the patient has a CYP2D6 impairment.

In some embodiments of the methods of the disclosure, the patient weighs ≥40 kg, for example, 40, 45, 50, 55, 60, 65, 70, 75, 80, 85, 90, 95, 100, 105, 110, 115, 120, 125, 130, 135, 140, 145, or about 150 kg, and the patient is administered a daily amount of deutetrabenazine of less than or equal to about 48 mg if the patient does not have a CYP2D6 impairment; or the patient is administered a daily amount of deutetrabenazine of less than or equal to about 36 mg if the patient has a CYP2D6 impairment.

Specific embodiments of the present disclosure include:

1) A method of treating dyskinesia in cerebral palsy in a human patient comprising administering to the patient a therapeutically effective amount of a compound having the Formula (I) or Formula (II) or a combination thereof:

(I)

(II)

or pharmaceutically acceptable salt thereof, wherein each position represented as D has deuterium enrichment of no less than about 10%.

2) The method of Embodiment 1, wherein each position represented as D has a deuterium enrichment of no less than about 20%.

3) The method of Embodiment 1, wherein each position represented as D has a deuterium enrichment of no less than about 50%.

4) The method of Embodiment 1, wherein each position represented as D has a deuterium enrichment of no less than about 70%.

5) The method of Embodiment 1, wherein each position represented as D has a deuterium enrichment of no less than about 80%.

6) The method of Embodiment 1, wherein each position represented as D has a deuterium enrichment of no less than about 90%.

7) The method of Embodiment 1, wherein each position represented as D has a deuterium enrichment of no less than about 98%.

8) The method of any one of Embodiments 1-7, wherein the compound is a compound having the Formula (I), or a pharmaceutically acceptable salt thereof.

9) The method of Embodiment 8, wherein the compound of the Formula (I) is deutetrabenazine.

10) The method of any one of Embodiments 1-7, wherein the compound is a compound having the Formula (II), or a pharmaceutically acceptable salt thereof.

11) The method of Embodiment 10, wherein the compound of Formula (II) is deuterated α-HTBZ or deuterated β-HTBZ.

12) The method of any one of Embodiments 1-11, wherein the administration of said compound results in a substantially increased maximum tolerated dose, decreased toxicity, increased half-life (t½), or lowered maximum plasma concentration (Cmax) of the minimum efficacious dose (MED), as compared to the administration of an equally efficacious dose of the corresponding non-deuterated compound.

13) The method of any one of Embodiments 1-12, wherein the dyskinesia is of dystonic type.

14) The method of any one of Embodiments 1-13, wherein the dyskinesia is of choreiform type.

15) The method of any one of Embodiments 1-14, wherein the human patient is a pediatric patient.

16) The method of any one of Embodiments 1-15, wherein the patient is between 6 and 18 years of age.

17) The method of any one of Embodiments 1-16, wherein the patient is further administered an additional therapeutic agent.

18) A method of treating dyskinesia in cerebral palsy in a human patient, comprising administering a daily amount of deutetrabenazine of about 6 mg/day to about 48 mg/day, in one or two doses, to the patient.

19) The method of Embodiment 18, wherein the treating results in maintaining or reducing the patient's abnormal involuntary movements associated with DCP, relative to the patient's abnormal involuntary movements at baseline.

20) The method of Embodiment 19, wherein the treating results in a reduction in the patient's abnormal involuntary movements associated with DCP, relative to the patient's abnormal involuntary movements at baseline.

21) The method of Embodiments 19-20, wherein the abnormal involuntary movements are measured by at least one of the rating scales:
a) the MD-CRS part II;
b) the MD-CRS part I;
c) the CaGI-I; and
d) the CGI-I.

22) The method of Embodiment 21, wherein the reduction in abnormal involuntary movements is demonstrated by at least one of:
a) a reduction in the MD-CRS part II score from baseline to week 15;
b) reduction in the MD-CRS part I score from baseline to week 15;
c) reduction in the CaGI-I score from baseline to week 15; and
d) reduction in the CGI-I score from baseline to week 15.

23) The method of Embodiment 21 or Embodiment 22 wherein the patient has a total score of ≥10 on the MD-CRS part II at baseline.

24) The method of any one of Embodiments 20-23, wherein the severity of the patient's abnormal involuntary movements is reduced relative to the severity of the patient's abnormal involuntary movements at baseline.

25) The method of any one of Embodiments 20-24, wherein the patient's motor function is improved relative to the patient's motor function at baseline.

26) The method of Embodiment 25, wherein the motor function is in the eye and periorbital region, face, tongue and perioral region, neck, trunk, upper limb, or lower limb or any combination thereof.

27) The method of any one of Embodiments 20-26, wherein the patient's oral/verbal function is improved, relative to the patient's oral/verbal function at baseline.

28) The method of any one of Embodiments 20-27, wherein the patient's ability for self-care is improved, relative to the patient's ability for self-care at baseline.

29) The method of any one of Embodiments 20-28, wherein the patient's attention/alertness is improved, relative to the patient's attention/alertness at baseline.

30) The method of any one of Embodiments 20-29, wherein the patient's abnormal involuntary movements are much or very much improved, relative to the patient's abnormal involuntary movements at baseline.

31) The method of any one of Embodiments 18-30, wherein the patient has a score of 4 or greater in the Clinical Global Impression of Severity (CGI-S) rating scale at baseline.

32) The method of any one of Embodiments 20-31, wherein the abnormal involuntary movements associated with dyskinesia in cerebral palsy are reduced by at least 20% relative to the patient's abnormal involuntary movements at baseline.

33) The method of any one of Embodiments 20-32, wherein the patient exhibits a reduction in the MD-CRS part II total score of at least 0.5 points, relative to baseline.

34) The method of any one of Embodiments 20-32, wherein the patient exhibits a reduction in the MD-CRS part II total score of at least 1 point, relative to baseline.

35) The method of any one of Embodiments 20-32, wherein the patient exhibits a reduction in the MD-CRS part II total score of at least 2 points, relative to baseline.

36) The method of any one of Embodiments 20-32, wherein the patient exhibits a reduction in the MD-CRS part II total score of at least 3 points, relative to baseline.

37) The method of any one of Embodiments 20-32, wherein the patient exhibits a reduction in the MD-CRS part II total score of at least 4 points, relative to baseline.

38) The method of any one of Embodiments 20-37, wherein the patient exhibits a reduction in the MD-CRS part I total score of at least 2 points, relative to baseline.

39) The method of any one of Embodiments 20-37, wherein the patient exhibits a reduction in the MD-CRS part I total score of at least 3 points, relative to baseline.

40) The method of any one of Embodiments 20-37, wherein the patient exhibits a reduction in the MD-CRS part I total score of at least 4 points, relative to baseline.

41) The method of any one of Embodiments 20-40, wherein the patient exhibits a reduction in the CaGI-I score of at least 0.5 points relative to baseline.

42) The method of any one of Embodiments 20-40, wherein the patient exhibits a reduction in the CaGI-I score of at least 0.6 points relative to baseline.

43) The method of any one of Embodiments 20-40, wherein the patient exhibits a reduction in the CaGI-I score of at least 0.7 points relative to baseline.

44) The method of any one of Embodiments 20-43, wherein the patient exhibits a reduction in the CGI-I Scale of at least 0.5 points relative to baseline.

45) The method of any one of Embodiments 20-43, wherein the patient exhibits a reduction in the CGI-I Scale of at least 0.6 points relative to baseline.

46) The method of any one of Embodiments 20-43, wherein the patient exhibits a reduction in the CGI-I Scale of at least 0.7 points relative to baseline.

47) The method of any one of the preceding Embodiments, wherein the patient weighs at least 12 kg at baseline.

48) The method of Embodiment 47, wherein the patient weighs 12 kg to <17 kg at baseline and wherein the daily amount of deutetrabenazine administered is less than or equal to about 24 mg if the patient does not have a CYP2D6 impairment; or less than or equal to about 12 mg if the patient has a CYP2D6 impairment.

49) The method of Embodiment 47, wherein the patient weighs 17 kg to <30 kg at baseline and wherein the daily amount of deutetrabenazine administered is less than or equal to about 30 mg if the patient does not have a CYP2D6 impairment; or less than or equal to about 18 mg if the patient has a CYP2D6 impairment.

50) The method of Embodiment 47, wherein the patient weighs 30 kg to <40 kg at baseline and wherein the daily amount of deutetrabenazine administered is less than or equal to about 42 mg if the patient does not have a CYP2D6 impairment; or less than or equal to about 24 mg if the patient has a CYP2D6 impairment.

51) The method of Embodiment 47, wherein the patient weighs ≥40 kg at baseline and wherein the daily amount of deutetrabenazine administered is less than or equal to about 48 mg if the patient does not have a CYP2D6 impairment; or less than or equal to about 36 mg if the patient has a CYP2D6 impairment

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the disclosure.

Example 1: Efficacy Study

A Phase 3, 21-week, multicenter, randomized, double-blind, placebo-controlled, parallel group study to evaluate the efficacy and safety of deutetrabenazine is performed as follows.

Approximately 185 patients are randomized to deutetrabenazine versus placebo in a 2:1 ratio (approximately 124 in the deutetrabenazine group; approximately 61 in the placebo group) stratified by age at baseline (6 to <12 years; 12 through 18 years, inclusive) and region (United States [US]; non-US). The sample size is re-estimated in an interim analysis (IA) and may be adjusted up to a total of approximately 230 patients.

The study population consists of male and female patients, 6 through 18 years of age inclusive, diagnosed with DCP.

Patients may be included in the study only if they meet all of the following criteria:
1. Patient is 6 through 18 years of age (inclusive) at baseline.
2. Patient weighs at least 26 pounds (12 kg) at baseline.
3. Patient has had cerebral palsy (CP) symptoms since infancy (≤2 years), and CP is judged by the investigator to be of a nonprogressive nature (Monbaliu E, et al. Clinical presentation and management of dyskinetic cerebral palsy. Lancet Neurol 2017;16(9):741-9; Wimalasundera N, Stevenson VL. Cerebral palsy. Pract Neurol 2016;16:184-194, the entireties of which are incorporated by reference herein).
4. Patient has a diagnosis of DCP according to the Surveillance of Cerebral Palsy in Europe criteria (Cans, C. Surveillance of cerebral palsy in Europe: a collaboration of cerebral palsy surveys and registers. Developmental Medicine & Child Neurology 2000;42:816-24, the entirety of which is incorporated by reference herein).
5. Patient has a total score of ≥10 on the MD-CRS part II items at the baseline visit, based on investigator scoring of chorea.
6. Patient's symptoms are causing functional problems determined by a Clinical Global Impression of Severity (CGI-S) score of 4 or greater based on investigator scoring.
7. Choreiform is the predominant movement disorder as assessed by the EAB at screening.
8. Patient is able to swallow study medication whole.
9. Patient and caregiver/adult are willing to adhere to the medication regimen and to comply with all study procedures.
10. Patient is in good general health, as indicated by medical and psychiatric history, as well as physical and neurological examination.
11. In the investigator's opinion, the patient and caregiver/adult have the ability to understand the nature of the study and its procedures, and the patient is expected to complete the study as designed.
12. Patient and caregiver/adult provided written informed consent according to local regulations (e.g., for patients/adolescents, the patient has provided written assent and/or co-consent for patients 14 years of age and older, as appropriate).
13. Females who are postmenarchal or ≥12 years of age may be included only if they have a negative beta-human chorionic gonadotropin test at baseline or are sterile.
14. Females who are postmenarchal or ≥12 years of age whose male partners are potentially fertile (i.e., no vasectomy) must use highly effective birth control methods for the duration of the study (i.e., starting at screening) and for 30 days after the last dose of IMP.

Patients will be excluded from participating in this study if they meet any of the following criteria:
1. a. Patient has a predominant movement disorder other than dyskinesia.
   b. Patient's predominant motor symptoms are dystonic.
   c. Patient's predominant motor symptoms are spastic.
   d. Patient has another movement disorder that could impair the motor assessment in the MD-CRS part II.
   e. Patient has choreiform movement disorder that has not been consistent throughout the life of the patient.
2. Patient has clinically significant depression at screening or baseline. Patients receiving antidepressant therapy may be enrolled if on a stable dose for at least 6 weeks before screening.
3. Patient has a history of suicidal intent or related behaviors within 2 years of screening:
   Previous intent to act on suicidal ideation with a specific plan, irrespective of level of ambivalence, at the time of suicidal thought
   Previous suicidal preparatory acts or behavior
4. Patient has a history of a previous actual, interrupted, or aborted suicide attempt.
5. Patient has a first-degree relative who has completed suicide.
6. Patient who is currently receiving or who, in the last 4 months before screening, has received botulinum neurotoxin (BoNT) in an investigational clinical trial.
   Patients may be included in the study if they have at least 2 treatments of Food and Drug Administration-approved BoNT at a regular interval (e.g., every 3 to 4 months), in reasonably stable dosages and locations (subject to investigator's judgement) to treat lower limb spasticity or dystonia, and if they are expected to continue this stable regimen of BoNT injections for the duration of this study. The patient is expected to continue on this stable regimen of BoNT injections on a regularly scheduled interval every 3 months for the duration of this study. The injection for spasticity or dystonia must be in a muscular region that is separate from the main areas affected by choreiform movement disorder.
   Patients who received BoNT injections more than 4 months before screening and who do not plan to continue these injections may be considered for this study.
7. Patient has received any of the following concomitant medications for dystonia or chorea within the specified exclusionary windows of screening:
   Within 3 months: depot neuroleptics
   Within 30 days: tetrabenazine, deutetrabenazine, or valbenazine
   Within 21 days: reserpine
   Within 14 days: neuroleptics (oral), typical and atypical antipsychotics, metoclopramide, levodopa, dopamine agonists, and monoamine oxidase inhibitors
   Use of benzodiazepines, muscle relaxants, trihexyphenidyl, baclofen (oral and intrathecal), gabapentin, and levetiracetam is allowed if the dosing has been stable for at least 4 weeks before screening.
   Use of topiramate (up to 200 mg/day) is allowed if dosing has been stable for at least 4 weeks before screening.
8. Patient has received treatment with stem cells, deep brain stimulation, transmagnetic stimulation, or transcranial direct current stimulation for treatment of abnormal movements or CP within 6 months of the screening visit, or the patient is not in a stable clinical condition.
9. Patient has recent surgical procedure or is anticipated to have a surgical procedure during the study that, in the opinion of the investigator, makes the patient unsuitable for the study.
10. Patient has a severe mental disability or an unstable or serious medical illness (e.g., epilepsy) at screening or baseline that, in the opinion of the investigator, could jeopardize or would compromise the patient's ability to participate in this study.

11. Patient has a QT interval corrected for heart rate using Fridericia's formula value >450 msec on 12-lead ECG at screening.
12. Patients with a history of torsade de pointes, congenital long QT syndrome, bradyarrhythmias, other cardiac arrhythmias, or uncompensated heart failure.
13. Patient has evidence of diminished hepatic function, as indicated by the following:

Aspartate aminotransferase (AST) or alanine aminotransferase (ALT) >2.5× the upper limit of the normal range (ULN) at screening Alkaline phosphatase (ALP) or total bilirubin >2×ULN at screening
Note: Patients with Gilbert's syndrome are eligible to participate if approved by the medical monitor.
Note: Patients with abnormalities in 2 or more of the following clinical laboratory parameters must be approved for enrollment by the medical monitor: AST, ALT, ALP, and total bilirubin.
14. Patient has evidence of clinically significant renal impairment, indicated by a serum creatinine >1.5×ULN at screening.
15. Patient has a known allergy to any of the components of the investigational medicinal product (IMP).
16. Patient has participated in an investigational drug or device study and received IMP/intervention within 30 days or 5 drug half-lives of screening, whichever is longer.
17. Patient is pregnant or breastfeeding.
18. Patient has a history of or acknowledges alcohol or substance abuse in the 12 months before screening, as defined in the Diagnostic and Statistical Manual of Mental Disorders (version 5).
19. Patient has a positive urine drug screen test result or is unable to refrain from substance abuse throughout the study.

Concomitant therapy or medication usage will be monitored throughout the study. The medications that are allowed are shown in the table, below. No dosing changes can be made during the study.

| Generic/Drug class | Condition |
| --- | --- |
| Stable medications allowed according to inclusion/exclusions criteria | |
| Hormonal birth control | Must be receiving stable treatment (including dose) for at least 3 months before screening |
| Antidepressants | Must be receiving stable treatment (including dose) for at least 6 weeks before screening |
| Benzodiazepines, muscle relaxants (including tizanidine), trihexyphenidyl, baclofen (oral and intrathecal), gabapentin, and levetiracetam | Primary use must not be for dyskinesia; dosing must have been stable for at least 4 weeks before screening. Note: PRN (as needed) use is prohibited. |
| Topiramate (up to 200 mg/day) | Must be receiving stable treatment (including dose) for at least 4 weeks before screening |
| Botulinum toxin | May be included in the study if they have at least 2 treatments of botulinum neurotoxin (BoNT) at a regular interval (eg, every 3 to 4 months), in reasonably stable dosages and locations (subject to investigator's judgement) to treat lower limb spasticity or dystonia, and if they are expected to continue this stable regimen of BoNT injections for the duration of this study. The injection for spasticity or dystonia must be in a muscular region that is separate from the main areas affected by choreiform movement disorder. |
| Additional medications allowed with preapproval from medical monitor | |
| Albuterol, levalbuterol | Asthma |
| Guaifenesin | Cold symptoms |
| Antihistamines | Allergies |
| Melatonin | Insomnia |
| | Allowed strong CYP inhibitors[a] |
| Bupropion | Antidepressant (aminoketone) |
| Fluoxetine | Antidepressant (selective serotonin reuptake inhibitor) |
| Stable medications allowed according to inclusion/exclusions criteria | |
| Paroxetine | Antidepressant (selective serotonin reuptake inhibitor) |

[a]The use of these medications will affect the maximum daily dose of study medication.
CYP = cytochrome P450; PRN = as needed.

The medical monitor will be contacted if a patient is receiving (or has to begin or stop receiving during the study) a medication that is associated with QTc prolongation or that is a known strong CYP inhibitor. The following medication usage is prohibited during the study. Prohibited medications that are associated with QTc prolongation are Azithromycin (up to 500 mg/day is allowed), Chloroquine/Mefloquine, Clarithromycin (systemic use prohibited; topical use is allowed), Domperidone, Droperidol, Erythromycin (systemic use prohibited; topical use is allowed), Moxifloxacin, Sevoflurane, Probucol, and Sparfloxacin. Prohibited antipsychotic medications are Chlorpromazine, Haloperidol, Loxapine, Molindone, Perphenazine, Pimozide, Prochlorperazine, Thioridazine, Thiothixene, Trifluoperazine, Promethazine-containing compounds, Carbamazepine, Aripiprazole, Asenapine maleate, Clozapine, Iloperidone, Lurasidone, Olanzapine, Olanzapine/fluoxetine, Paliperidone, Quetiapine, Risperidone, Ziprasidone, and Tiapride.

The primary and secondary study objectives and measures/endpoints are the following:

| Objectives | Measures/Endpoints |
|---|---|
| The primary objective of the study is to evaluate the efficacy of deutetrabenazine to reduce the severity of dyskinetic involuntary movements associated with CP. | The primary efficacy endpoint is the change from baseline to week 15 in the MD-CRS part II total score (movement disorder severity, centrally read) (deutetrabenazine versus placebo). |
| A secondary objective is to evaluate the specific efficacy parameters of deutetrabenazine beyond the measure of the primary objective. | The key secondary efficacy endpoints (deutetrabenazine versus placebo) are the following:<br>    MD-CRS part I total score (general assessment, centrally read) change from baseline to week 15<br>    CaGI-I Scale (global, caregiver rated) at week 15<br>    CGI-I Scale (global, physician rated) at week 15<br>Other efficacy measures and endpoints (deutetrabenazine versus placebo) include the following:<br>    MD-CRS Global Index (calculated as a sum of MD-CRS Index I and Index II)<br>    UHDRS-TMS<br>    UHDRS-TMC<br>    UHDRS-TMD<br>    PEDI-CAT (ADL, parent/caregiver completed, counterbalanced version)<br>    The CP module of the PedsQL (QoL, patient/caregiver)<br>    PGI-I Scale (global, patient/caregiver)<br>    CGI-S Scale (global, physician rated)<br>    CaGI-I response, defined as patients who are described by the caregiver as "Much Improved" or "Very Much Improved" in the CaGI-I score<br>    CGI-I response, defined as patients who are described as "Much Improved" or "Very Much Improved" in the CGI-I score<br>    CGI-S response, defined as patients who have a reduction of ≥1 point in the CGI-S score<br>    PGI-I response, defined as patients who are described as "Much Improved" or "Somewhat Improved" in the PGI-I score |
| A secondary objective of the study is to evaluate the safety and tolerability of deutetrabenazine. | The safety variables include adverse events (and the number of patients who withdraw from the study due to adverse events), vital signs, laboratory tests (hematology, chemistry, and urinalysis), ECG measurements, and the children's C-SSRS. |

ADL = activities of daily living; CaGI-I = Caregiver Global Impression of Improvement; CGI-I = Clinical Global Impression of Improvement; CGI-S = Clinical Global Impression of Severity; CP = cerebral palsy; C-SSRS = Columbia-Suicide Severity Rating Scale; ECG = electrocardiogram; MD-CRS I and II = Movement Disorder-Childhood Rating Scale Index I and Index II; PEDI-CAT = Pediatric Evaluation Disability Inventory-Computer Adapted Test; PedsQL = Pediatric Quality of Life Inventory; PGI-I = Patient Global Impression of Improvement; QoL = quality of life; UHDRS-TMC = Unified Huntington's Disease Rating Scale-Total Maximal Chorea; UHDRS-TMD = Unified Huntington's Disease Rating Scale-Total Maximal Dystonia; UHDRS-TMS = Unified Huntington's Disease Rating Scale-Total Motor Score.

General Study Design:

This is a Phase 3, 21-week, multicenter, randomized, double-blind, placebo-controlled, parallel group study to evaluate the efficacy and safety of deutetrabenazine administered as oral tablets at a starting dose of 6 mg once daily in patients (age 6 through 18 years) with DCP with predominant choreiform movement disorder, who have had cerebral palsy (CP) symptoms, of a nonprogressive nature, since infancy (≤2 years of age). The study will consist of a screening period (up to 31 days) and a double-blind treatment period including a titration period (7 weeks) and a maintenance period (8 weeks), followed by a washout period of 1 week, and a follow-up telephone contact 1 week after the washout period. Throughout the study, patients will interact regularly with investigational center personnel, in-clinic and by telephone (with non-recording live video), for the evaluation of safety/tolerability, dyskinesia severity, and behavioral status (in-clinic only).

At the baseline visit (day 1), patients will be randomly assigned to 1 of 2 treatment groups with deutetrabenazine investigational medicinal product ("IMP") or placebo IMP in a 2:1 ratio stratified by age at baseline (6 to <12 years; 12 through 18 years, inclusive) and region (US; non-US). IMP will be titrated during the double-blind treatment period starting with 6 mg of deutetrabenazine or matching placebo IMP in the morning of days 2 and 3, followed by evening administration starting on day 3 for the remainder of the week (if body weight is ≥40 kg/88 lbs). Deutetrabenazine daily doses of 12 mg and higher will be administered as 2 divided equal doses, approximately 8 to 10 hours apart during the day. The number of matching placebo IMP tablets will be increased accordingly. After week 1, dose increases may not occur more frequently than every 5 days. During the titration period, the dose of IMP will be adjusted according to the titrations scheme to identify a dose level that optimally reduces dyskinesia (as determined by the investigator, as indicated by a reduction in the Clinical Global Impression of Improvement [CGI-I]) and is well tolerated. If a patient experiences a "clinically significant" adverse event attributable to the IMP, the investigator will first determine if a dose reduction (to the previous dose level) or suspension is necessary and possible. After titration, patients will remain at their optimal dose for the length of the maintenance period.

Screening period (up to 31 days): After informed consent (and written assent and/or co-consent, as appropriate) is obtained, patients who are stable from a medical and psychiatric standpoint will undergo a screening evaluation, including medical history, physical and neurological examination, laboratory testing, 12-lead electrocardiogram (ECG), along with MD-CRS part I and part II assessments (video recorded, centrally read by Enrollment Adjudication Board [EAB]), to assess severity of dyskinesia, comorbid CP symptoms, and behavioral status. Screening may be conducted over 2 separate visits at the discretion of the investigator. The diagnosis of CP and DCP will be established based on clinical features as described in the inclusion/exclusion criteria. The EAB will also confirm, based on video recordings, that choreiform is clinically the predominant movement disorder of the patient's DCP. EAB assessment results will be available to the investigator prior to baseline and randomization. At all other visits, the MD-CRS part II rating scale will be administered by the investigational center physician and video recorded for central-blinded reading.

Titration period (7 weeks): Patients who remain eligible for participation in the study will be randomized at the baseline visit (day 1) and instructed to take the first dose of blinded IMP the following morning, without regard to food. The titration scheme and maximum dose will be determined by body weight and cytochrome P450 2D6 (CYP2D6) impairment status at baseline. Patients will be classified as CYP2D6 impaired if they are receiving a strong CYP2D6 inhibitor or are a CYP2D6 poor metabolizer.

Test IMP will be administered as oral tablets at a starting dose of 6 mg once daily. Titration schemes based on body weight at baseline are shown in Tables 1 and 3:

TABLE 1

Maximum Daily Dose of IMP During the Titration Period by Day and Weight Category at Baseline

| Study day$^a$ | Daily dose | | | |
|---|---|---|---|---|
| | 12 kg to <17 kg (26 lbs to <37 lbs) | 17 kg to <30 kg (37 lbs to <66 lbs) | 30 kg to <40 kg (66 lbs to <88 lbs) | ≥40 kg (≥88 lbs) |
| Day 2 | 6 mg | 6 mg | 6 mg | 6 mg |
| Days 3-7 | 6 mg | 6 mg | 6 mg | 12 mg$^b$ |
| Days 8-14 | 6 mg | 12 mg | 12 mg | 18 mg |
| Days 15-21 | 12 mg$^c$ | 18 mg | 18 mg | 24 mg |
| Days 22-28 | 12 mg$^c$ | 18 mg$^c$ | 24 mg$^c$ | 30 mg |
| Days 29-35 | 18 mg$^c$ | 24 mg$^c$ | 30 mg$^c$ | 36 mg$^c$ |
| Days 36-42 | 18 mg$^c$ | 24 mg$^c$ | 36 mg$^c$ | 42 mg$^c$ |
| Days 43-49 | 24 mg$^c$ | 30 mg$^c$ | 42 mg$^c$ | 48 mg$^c$ |

$^a$Administration of a given dose will take place throughout the days indicated (inclusive), with the in-clinic visits occurring at days 1, 21, and 49.
$^b$Patients will receive the 6-mg once-daily dose in the morning on days 2 and 3, followed by evening administration of 6 mg starting on day 3.
$^c$For those taking strong CYP2D6 inhibitors, such as paroxetine, fluoxetine, and bupropion, or those who are poor CYP2D6 metabolizers, the maximum daily dose for patients ≥40 kg is 36 mg/day, that for 30 to <40 kg is 24 mg/day, that for 17 to <30 kg is 18 mg/day, and that for 12 to <17 kg is 12 mg/day (see Table 2).
CYP2D6 = cytochrome P450 2D6; IMP = investigational medicinal product.

TABLE 2

Maximum Daily Dose of IMP by CYP2D6 Impairment Status

| Weight category | Maximum daily dose in the absence of CYP2D6 impairment | Maximum daily dose in the presence of CYP2D6 impairment |
|---|---|---|
| 12 kg to <17 kg (26 lbs to <37 lbs) | 24 mg | 12 mg |
| 17 kg to <30 kg (37 lbs to <66 lbs) | 30 mg | 18 mg |
| 30 kg to <40 kg (66 lbs to <88 lbs) | 42 mg | 24 mg |
| ≥40 kg (≥88 lbs) | 48 mg | 36 mg |

CYP2D6 = cytochrome P450 2D6; IMP = investigational medicinal product.
Note:
Patients will be classified as CYP2D6 impaired if they are receiving a strong CYP2D6 inhibitor or are a CYP2D6 poor metabolizer. Strong CYP2D6 inhibitors include paroxetine, fluoxetine, and bupropion.

The maximum daily dose is determined by body weight at baseline and CYP2D6 impairment status.

Patients and their caregiver/adult will interact weekly with the investigator/staff, either by telephone contact (with non-recording live video) or clinic visit from week 1 through week 7 of the titration period, in order to evaluate safety/tolerability and establish a dose of IMP that optimally reduces the severity of dyskinetic involuntary movements (clinically meaningful reduction in dyskinesia, as indicated by a reduction in the CGI-I) and is well tolerated. Safety/tolerability in-clinic evaluations during titration include assessment of vital signs, monitoring for adverse events and concomitant medications, 12-lead ECGs, and rating scales for depression and suicidality. If a patient experiences a "clinically significant" adverse event attributable to the IMP, the investigator will first determine if a dose reduction (to the previous dose level) or suspension is necessary and possible. At the end of the titration period, the patient's dose will be established for the maintenance period.

In-person (in-clinic) study visits will be scheduled at weeks 3 and 7, and telephone contacts (with non-recording live video) will be scheduled for weeks 1, 2, 4, 5, and 6 in order to assess dyskinesia and adverse events. The telephone contacts to the patient will be supported by live video stream, without recording, to provide visual confirmation to the investigator of the verbal information provided by the patient or caregiver. The dose of the IMP should be increased on a weekly basis to reach a clinically meaningful reduction in dyskinesia, as indicated by a reduction in the CGI-I. The IMP dose should not be increased further if either of the following occurs:

the patient experiences a protocol-defined "clinically significant" adverse event (defined as an adverse event that is related to IMP and is either moderate or severe in intensity or meets the criteria for a serious adverse event), OR the maximum allowable dose is reached based on the patient's weight and CYP2D6 impairment status at baseline.

Dose adjustments can be made up to and including the week 7 in-clinic visit. If an optimal dose is reached before the week 7 in-clinic visit, the dose of IMP should not be increased further, but the patient should continue on that dose for the remainder of the titration period and throughout the maintenance period. If a patient experiences a "clinically significant" adverse event attributable to the IMP, the investigator will first determine if a dose reduction (to the previous dose level) or suspension is necessary and possible. If the determination that a patient requires a dose reduction or suspension is made during a telephone contact, an unscheduled clinic visit should be conducted as soon as practicable thereafter.

Maintenance period (8 weeks): Patients will continue to receive their maintenance dose over the next 8 weeks, although a 1-time dose reduction (to the previous dose level for the remainder of the study) for adverse events is allowed. Patients will return to the clinic at weeks 9, 12, and 15 for assessments of efficacy and safety.

Washout period and follow-up: All patients will discontinue IMP at the week 15 visit and will return 1 week later for the end-of-study visit. Patients who complete the study may be eligible to begin participation in the open-label safety extension study. Patients not participating in the open-label safety extension study will have a follow-up telephone contact for safety evaluation 1 week after the end of the washout period (2 weeks after their last dose of IMP [week 17]).

When approximately 90 patients have completed the study (including follow-up), an independent Data Monitoring Committee (iDMC) will perform an unblinded IA for futility and sample size re-estimation based on centrally read MD-CRS part II. Based on the results of the IA, the study may be stopped or the sample size may be kept as planned (approximately 185 total patients) or increased (up to approximately 230 total patients). An iDMC charter will be developed for the IA, and the procedures to ensure the integrity of the study will be provided in the charter.

At the time of informed consent, the parent/legal guardian will be counseled that, once randomized to treatment, patients are to remain in the study and complete all study procedures unless the choice is made to withdraw consent. Patients who withdraw from the study before completing the 15-week treatment period should have an early termination (ET) visit as soon as possible after the last dose of IMP. All patients who discontinue early will have a follow-up telephone contact for safety evaluation 2 weeks after their last dose of IMP; evaluations will be as described for week 17.

Primary and Secondary Estimands:

The primary estimand is the difference in means between deutetrabenazine and placebo in the target patient population for the change from baseline to week 15 in centrally read MD-CRS part II, regardless of whether or not dose reduction, suspension, or discontinuation occurred, and regardless of treatment-related adverse events.

The secondary estimands are the differences in means between deutetrabenazine and placebo in the target patient population for (1) change from baseline to week 15 in centrally read Movement Disorder-Childhood Rating Scale part I (MD-CRS part I); (2) Caregiver Global Impression of Improvement (CaGI-I) at week 15; and (3) CGI-I at week 15, regardless of whether or not dose reduction, suspension, or discontinuation occurred, and regardless of treatment-related adverse events.

The primary estimand assesses the effectiveness in the reduction of choreiform movements in patients with DCP with predominant choreiform movement disorder, focusing on the causal effects attributable to the IMP. The secondary estimands assess the effectiveness on patients' ability to perform daily functions and the improvement in dyskinesia symptoms as evaluated by the caregiver and the investigator, with a focus on the causal effects attributable to the IMP.

The patient population for this study is patients with DCP with predominant choreiform movement disorder and severity of DCP represented by a total score of $\geq 10$ on the MD-CRS part II at baseline. This population is expected to have the sensitivity to demonstrate clinically meaningful improvement following treatment with deutetrabenazine. Due to practical reasons, it is not possible to obtain a central reading of MD-CRS part II items at the time of the baseline visit, prior to randomization, to determine if a patient is eligible for the study. Therefore, inclusion to the study is based on investigator scoring of MD-CRS part II items at baseline. Patients who do not meet the MD-CRS part II criterion based on central reading will be excluded from the primary analysis set (i.e., the modified intent-to-treat population [mITT], which includes only the patients who have a total score of $\geq 10$ on the MD-CRS part II items at the baseline visit, based on centrally read scoring).

Analysis of Primary Endpoint:

The primary endpoint is the change from baseline to week 15 in centrally read MD-CRS part II (deutetrabenazine versus placebo).

The mITT analysis (on all patients with centrally read total scores of $\geq 10$ on MD-CRS part II items at baseline, and at least 1 post-baseline centrally read MD-CRS II assessment) will be used for the primary analysis.

The primary analysis will be a mixed-model, repeated-measures with the change in MD-CRS part II total score as the dependent variable. The model will include fixed effects for treatment group, week (3 levels: weeks 9, 12, and 15), and treatment group by week interaction. The baseline MD-CRS part II total score, age group at baseline (2 levels: 6 to <12 years; 12 through 18 years), and region (US; non-US) will be included as covariates. The unstructured covariance model will be used.

Missing data will be classified as missing at random (MAR) and missing not at random (MNAR). Intermittent missing data and ET for patients who are lost to follow-up or who terminated for reasons that are not related to tolerability, adverse events, or lack of efficacy will be classified as MAR. All other early terminations will be classified as MNAR. Classification as MAR/MNAR will be done in a blinded manner prior to the IA and prior to database lock. The MAR/MNAR multiple imputation method will be applied in the primary analysis, where MNAR data will be imputed using the jump-to-reference method, and MAR data will be imputed based on the randomized treatment group. The resulting complete, imputed datasets will each be analyzed using the analysis model described above, and the resulting statistics combined using methodology presented byRubin DB. Multiple Imputation for Nonresponse in Surveys. 1987, New York: John Wiley & Sons) and Little R J A, Rubin D B. Statistical Analysis with Missing Data, Second Edition. 2002, New York: John Wiley & Sons, the entireties of which are incorporated by reference herein.

The difference in least squares (LS) mean of the change in MD-CRS part II total score from baseline to week 15 (deutetrabenazine versus placebo) will be compared using a 1-sided test for superiority at a nominal significance level of $\alpha=0.025$.

The LS mean and standard error for the treatment groups, the LS mean difference, 2-sided 95% confidence interval, and p-value for the comparison (deutetrabenazine versus placebo) at week 15 will be presented.

Key Secondary Endpoints and Analysis:

The key secondary endpoints are the following:
1. Change from baseline to week 15 in centrally read MD-CRS part I (deutetrabenazine versus placebo)
2. CaGI-I at week 15 (deutetrabenazine versus placebo)
3. Clinical Global Impression of Improvement (CGI-I) at week 15 (deutetrabenazine versus placebo)

Each key secondary endpoint will be analyzed in the same fashion as the primary analysis, with the exception that the baseline value of the given endpoint will be included as the covariate.

Other Efficacy Measures/Endpoints:

Other efficacy measures and endpoints (deutetrabenazine versus placebo) include the following:
MD-CRS Global Index (calculated from MD-CRS part I and part II)
Unified Huntington's Disease Rating Scale-Total Motor Score (UHDRS-TMS)
Unified Huntington's Disease Rating Scale-Total Maximal Chorea (UHDRS-TMC)
Unified Huntington's Disease Rating Scale-Total Maximal Dystonia (UHDRS-TMD)
Pediatric Evaluation Disability Inventory-Computer Adapted Test (PEDI-CAT) (activities of daily living, parent/caregiver completed, counter-balanced version)
The CP module of the Pediatric Quality of Life Inventory (PedsQL) (quality of life, patient/caregiver)
Patient Global Impression of Improvement Scale ([PGI-I] global, patient/caregiver)
Clinical Global Impression of Severity ([CGI-S], global, physician rated)
CaGI-I response, defined as patients who are described by the caregiver as "Much Improved" or "Very Much Improved" in the CaGI-I score
CGI-I response, defined as patients who are described as "Much Improved" or "Very Much Improved" in the CGI-I score
CGI-S response, defined as patients who have a reduction of ≥1 point in the CGI-S score
PGI-I response, defined as patients who are described as "Much Improved" or "Somewhat Improved" in the PGI-I score Multiple Comparisons and Multiplicity:

The primary efficacy endpoint will be tested at the 1-sided significance level of $\alpha=0.025$.

If the primary endpoint is statistically significant (p-value ≤0.025), the 3 key secondary hypotheses will be tested using a hierarchical approach at the 1-sided significance level of $\alpha=0.025$, in the following order: (1) MD-CRS part I, (2) CaGI-I, and (3) CGI-I.

If the primary endpoint is not statistically significant, confirmatory hypothesis testing will not be carried out on the secondary hypotheses, and they will be considered exploratory rather than confirmatory.

If a secondary endpoint is not statistically significant, confirmatory hypothesis testing will not be carried out on the next secondary hypothesis/hypotheses, and it/they will be considered as exploratory rather than confirmatory.

No multiplicity control will be applied to the sensitivity analysis or other endpoints.

Planned Interim Analysis:

When approximately 90 patients have completed the study (including follow-up), an iDMC will perform an unblinded IA for futility and sample size re-estimation based on centrally read MD-CRS part II.

The sample size re-estimation will be performed using the promising zone approach (Mehta C R, Pocock S J. Adaptive increase in sample size when interim results are promising: a practical guide with examples. Stat Med 2011;30(28): 3267-84, the entirety of which is incorporated by reference herein). At the IA, the conditional power for the initially planned sample size of approximately 185 patients will be estimated given the observed data, and the sample size may be increased up to a total maximum of approximately 230 patients.

The Type I error rate will be controlled using the Chen, DeMets, and Lan method (Chen Y H, DeMets D L, Lan K K. Increasing the sample size when the unblinded interim result is promising. Stat Med 2004;23(7):1023-38, the entirety of which is incorporated by reference herein); hence, $\alpha=0.025$ will be used for the primary analysis.

Safety Analyses:

Safety analyses will be performed on the safety analysis set.

All adverse events will be coded using the Medical Dictionary for Regulatory Activities. Each patient will be counted only once in each preferred term or system organ class category for the analyses of safety. Summaries will be presented for all adverse events (overall and by severity), adverse events determined by the investigator to be related to test IMP (i.e., reasonable possibility) (defined as related or with missing relationship) (overall and by severity), serious adverse events, and adverse events causing withdrawal from the study. Summaries will be presented by treatment group and for all patients. Patient listings of serious adverse events and adverse events leading to withdrawal will be presented.

Changes in laboratory, ECG, and vital signs measurements data will be summarized descriptively. All values will be compared with predefined criteria to identify potentially clinically significant values or changes, and such values will be listed.

The use of concomitant medications will be summarized by therapeutic class using descriptive statistics.

The frequency and severity of suicidal ideation or behavior according to the children's Columbia-Suicide Severity Rating Scale (C-SSRS) questionnaire will be presented for all patients aged ≥12 years by visit and by treatment group. A shift table for children's C-SSRS categories at baseline, compared to the worst (highest) category during the treatment period, will be presented.

Drug-induced parkinsonism will be evaluated according to the Extrapyramidal Symptom Rating Scale (ESRS) (subscales I (subjective questionnaire) and II (evaluation for parkinsonism/akathisia)). (See, e.g., Chouinard G, Margolese H C. Manual for the Extrapyramidal Symptom Rating Scale (ESRS). Schizophrenia Research 2005;76:247-65, the entirety of which is incorporated by reference herein). The ESRS is administered at screening; baseline; and weeks 3, 7, 9, 12, 15/ET, and 16/EOS. The subscale I of the ESRS questionnaire rates subjective parkinsonism/akathisia at periods other than the day of examinations during the last 7 days. It is scored on a 4-point scale (0=Absent, 1=Mild, 2=Moderate, or 3=Severe). The evaluation takes into account the verbal report of the patient on: 1) the frequency and duration of the symptom during the day, 2) the number of days the symptom was present during the last week, and 3) the subjective evaluation of the intensity of the symptom by the patient. The subscale II of the ESRS questionnaire for evaluation of parkinsonism and akathisia includes 17 items with scores ranging from 0-102 to assess the following: tremor (0-48), gait and posture (0-6), postural stability (0-6), rigidity (0-24), expressive automatic movements (0-6), bradykinesia (0-6), and akathisia (0-6).

Assessment of change in behavior will be performed according to the Child Behavior Checklist (CBCL) questionnaire. See, e.g., Achenbach T M, Ruffle T M. The Child Behavior Checklist and related forms for assessing behavioral/emotional problems and competencies. Pediatr Rev 2000;21(8):265-71; Achenbach T M. Advancing assessment of children and adolescents: commentary on evidence-based assessment of child and adolescent disorders. J Clin Child Adolesc Psychol 2005;34:541-7, the entireties of which are incorporated by reference herein. The full CBCL has two parts, a Competence Scale (Parts Ito VII) and a Syndrome Scale (behavioral items). The Competence Scale (Parts Ito VII) assesses various activities (e.g., sports, hobbies, games, organizations, clubs, teams, groups, jobs, and chores), interpersonal relationships, and academic performance. The Syndrome Scale comprises 118 questions related to problem behaviors. This study will use a recall period of "now or within the last week," representing a modification from the original scale, which was "now or within the last 6 months". For each item, the parent/caregiver will circle 0 if the item is not true of their child, 1 if the item is somewhat or sometimes true, and 2 if the item is very true or often true. The CBCL is part of the Achenbach System of Empirically Based Assessment that identifies syndromes that are behavioral clusters that indicate certain types of behavioral, social, or emotional problems. The problem behaviors are scored on the following 8 empirically based syndromes: anxious/depressed, withdrawn/depressed, somatic complaints, social problems, thought problems, attention problems, rule-breaking behavior, and aggressive behavior. The Competence and Syndrome Scales are displayed on profiles in relation to gender and age-specific percentiles and T scores based on national normative samples. The full CBCL assessment (Competence and Syndrome Scales) will be completed at screening and at week 15/ET. Only the CBCL Syndrome scale will be completed at baseline, weeks 3, 7, 9, 12, and 16/EOS.

Assessment of sedation will be performed according to the Epworth Sleepiness Scale (ESS) questionnaire. (See, e.g., Johns M W. The assessment of sleepiness in children and adolescents. Sleep Biol Rhythm 2015;13 (Suppl. 1): 97, the entirety of which is incorporated by reference herein). The ESS is a self-administered questionnaire composed of 8 questions that provide a measure of a patient's general level of daytime sleepiness. The ESS is administered at screening; baseline; and weeks 3, 7, 9, 12, 15/ET, and 16/EOS. The ESS asks respondents to rate, on a 4-point Likert scale (0-3; 0=would never fall asleep; 1=slight chance of falling asleep; 2=moderate chance of falling asleep; 3=high chance of falling asleep), their usual chances of dozing off or falling asleep in different situations or activities that most people engage in as part of their daily lives. The total ESS score is the sum of 8 item scores and can range between 0 and 24 with the higher the score indicating a higher level of daytime sleepiness.

For continuous variables, descriptive statistics will be provided for actual values and changes from baseline to each time point. For categorical variables, patient counts and percentages will be provided. Descriptive summaries of serious adverse events, patient withdrawals due to adverse events, and potentially clinically significant abnormal values (clinical laboratory or vital signs) based on predefined criteria will be provided as well.

If any patient dies during the study, a listing of deaths will be provided, and all relevant information will be discussed in the patient narrative included in the clinical study report.
Tolerability Analysis:

If more than 15% of the patients withdraw from the study before the end of the treatment period, the number of days until study discontinuation will be analyzed using Kaplan-Meier methodology using the ITT analysis set.
Pharmacokinetic/Pharmacodynamic Analysis:

Samples collected for pharmacokinetic analysis will be quantified for Deutetrabenazine and alpha-dihydrotetrabenazine (α-HTBZ) and beta-dihydrotetrabenazine (β-HTBZ) as active metabolites of deutetrabenazine, and other metabolites, as required. The sum of α-HTBZ and β-HTBZ will be calculated from the individual concentrations. Concentrations of deutetrabenazine and metabolites (individually and as sum) may be analyzed using population pharmacokinetic techniques. Exploratory pharmacokinetic/pharmacodynamic analysis may be performed on pharmacodynamic/safety endpoints using all relevant accumulated pharmacokinetic/pharmacodynamic data from deutetrabenazine studies.
Results Treatment with deutetrabenazine is shown to be safe and effective. Treatment with deutetrabenazine results in significant improvements in all primary and secondary endpoints.

Patients receiving deutetrabenazine demonstrate a significant reduction in the MD-CRS part II total score of about 0.5-4 points (versus placebo) from baseline to week 15, thereby demonstrating an improvement in DCP attributable to the deutetrabenazine.

Patients receiving deutetrabenazine also demonstrate a significant reduction in the MD-CRS part I total score of about 2-4 points (versus placebo) from baseline to week 15, thereby demonstrating an improvement in DCP attributable to the deutetrabenazine.

Patients receiving deutetrabenazine also demonstrate a significant reduction in the CaGI-I score of about 0.5-0.7 points (versus placebo) from baseline to week 15, thereby demonstrating an improvement in DCP attributable to the deutetrabenazine.

Patients receiving deutetrabenazine also demonstrate a significant reduction in the CGI-I score of about 0.5-0.7 points (versus placebo) from baseline to week 15, thereby demonstrating an improvement in DCP attributable to the deutetrabenazine.

Patients receiving deutetrabenazine also demonstrate improvement based on significant reductions in Unified Huntington's Disease Rating Scale-Total Motor Score (UHDRS-TMS), or Unified Huntington's Disease Rating Scale-Total Maximal Chorea (UHDRS-TMC), or Unified Huntington's Disease Rating Scale-Total Maximal Dystonia (UHDRS-TMD), or the CP module of the Pediatric Quality of Life Inventory (PedsQL) (quality of life, patient/caregiver).

Patient's receiving deutetrabenazine also demonstrate improvement based on the Pediatric Evaluation Disability Inventory-Computer Adapted Test (PEDI-CAT) (activities of daily living, parent/caregiver completed, content-balanced version).

Patient's receiving deutetrabenazine also demonstrate a CaGI-I response, defined as patients who are described by the caregiver as "Much Improved" or "Very Much Improved" in the CaGI-I score.

Patient's receiving deutetrabenazine also demonstrate a CGI-I response, defined as patients who are described as "Much Improved" or "Very Much Improved" in the CGI-I score.

Patient's receiving deutetrabenazine also demonstrate a CGI-S response, defined as patients who have a reduction of >1 point in the CGI-S score.

Patient's receiving deutetrabenazine also demonstrate a PGI-I response, defined as patients who are described as "Much Improved" or "Somewhat Improved" in the PGI-I score.

The deutetrabenazine treatment will be shown to be safe as by the children's Columbia-Suicide Severity Rating Scale (C-SSRS), the Extrapyramidal Symptom Rating Scale (ESRS), the Child Behavior Checklist (CBCL), the Epworth Sleepiness Scale (ESS), and the lack of serious adverse events.

Example 2: Open-Label Extension Study

A Phase 3, 55-week, open-label, single-arm, long-term safety, tolerability, and efficacy study of deutetrabenazine for the treatment of dyskinesia in cerebral palsy in children and adolescents is performed as follows:

General Study Design: patients who have successfully completed the Phase 3, 21-week, multicenter, randomized, double-blind, placebo-controlled, parallel group study to evaluate the efficacy and safety of deutetrabenazine ("the parent study") may be eligible to enroll in this study after they complete a 1-week washout period and the final evaluation at week 16. This study will include children and adolescents between 6 and 18 years of age at the time when they enrolled in the parent study.

Screening: Screening evaluations for this open-label study will be performed as part of the baseline visit. Any adverse event that started after the end of the parent study and is recorded after informed consent/assent for this open-label study will be captured within this study.

Day 1 visit: For all patients, the week 16 visit from the parent study may be the day 1 visit for the open label study. Day 1 assessments for the open label study that are identical to the parent study week 15/16 visit assessments, whichever is the most current, do not need to be repeated, except for orthostatic pulse rate and blood pressure, which need to be repeated at day 1.

Titration period (7 weeks): Because the patients from parent study have discontinued deutetrabenazine treatment for at least 1 week at completion of the parent study or received placebo in the parent study, all patients will undergo deutetrabenazine dose titration in this study in order to maintain the blind of the parent study. Patients will receive 6 mg of deutetrabenazine on the morning of day 2. The titration scheme and maximum dose follows the one in the parent study.

Maintenance period (46 weeks): At the end of the titration period, the patient's initial dose for the maintenance period (week 8 to week 53) will be established. Dose adjustments of deutetrabenazine (upward or downward) may be made during the maintenance period, if necessary, but not more often than every 5 days and only in increments of 6 mg. As during titration, dose adjustments should be made based on all available information. Dose reductions of deutetrabenazine or suspensions of patients for adverse events or tolerability findings are allowed. During the maintenance period, in-person (in-clinic) study visits will be scheduled at weeks 14, 27, 40, and 53 for assessments of safety and efficacy, and telephone contacts (with non-recording live video) will be scheduled for weeks 21, 33, and 46 in order to assess adverse events and dyskinesia. At week 53/early termination (ET), patients will undergo a complete evaluation, including vital signs and weight, physical and neurological examination, height measurement, 12-lead ECG, safety laboratory testing, urine drug screen, and beta-human chorionic gonadotropin (β-HCG) test, when applicable, as well as the MD-CRS parts I and II, CaGI-I, CGI-I, CGI-S, PEDI-CAT, UHDRS-TMS, COPM, children's C-SSRS assessments, ESRS (subscales I and II), CBCL, and ESS.

Washout and follow-up period: All patients will discontinue deutetrabenazine at the week 53 visit and will return 1 week later (week 54) for evaluation of safety. Patients will have a follow-up telephone contact (no live video streaming) for safety evaluation 1 week after the end of the washout period (2 weeks after their last dose of deutetrabenazine (week 55).

The primary and secondary study objectives and measures/endpoints are the following:

| Objectives | Measures/Endpoints |
| --- | --- |
| The primary objective of this study is to evaluate the safety and tolerability of long-term therapy with deutetrabenazine in children and adolescents with DCP. | The safety measures/endpoints are as follows:<br>adverse events<br>vital signs<br>children's C-SSRS<br>ECG parameters<br>clinical laboratory parameters (hematology, serum chemistry, and urinalysis)<br>ESRS (subscales I and II)<br>CBCL<br>ESS |
| The secondary objective of this study is to evaluate the efficacy of long-term therapy with deutetrabenazine in reducing the severity of DCP | The efficacy measures/endpoints are as follows:<br>MD-CRS part I total score (physician rated)<br>MD-CRS part II total score (physician rated)<br>MD-CRS Global Index (calculated from MD-CRS parts I and II total scores)<br>CaGI-I (global, caregiver rated)<br>CGI-I (global, physician rated)<br>CGI-S (global, physician rated) |

| Objectives | Measures/Endpoints |
|---|---|
| | PEDI-CAT (activities of daily living, caregiver completed, content-balanced version)<br>UHDRS-TMS (physician rated)<br>COPM (physician rated) |

CaGI-I = Caregiver Global Impression of Improvement; CBCL = Child Behavior Checklist (for ages 6 to 18); CGI-I = Clinical Global Impression of Improvement; CGI-S = Clinical Global Impression of Severity; COPM = Canadian Occupational Performance Measure; C-SSRS = Columbia-Suicide Severity Rating Scale; DCP = dyskinesia in cerebral palsy; ECG = electrocardiogram; ESRS = Extrapyramidal Symptom Rating Scale (subscales I and II); ESS = Epworth Sleepiness Scale (for children and adolescents); MD-CRS = Movement Disorder-Childhood Rating Scale; PEDI-CAT = Pediatric Evaluation Disability Inventory-Computer Adapted Test; UHDRSTMS = Unified Huntington's Disease Rating Scale-Total Motor Score.

Patients may be included in the study only if they meet all of the following criteria:
1. Patient has completed parent Study (Example 1, supra).
2. Patient weighs at least 12 kg (26 lb) on day 1 of this study.
3. Patient is able to swallow deutetrabenazine tablet whole.
4. Patient and caregiver are willing to adhere to deutetrabenazine regimen and comply with all study procedures.
5. Patient is in good general health, as indicated by medical and psychiatric history and physical and neurological examination.
6. In the investigator's opinion, the patient and caregiver have the ability to understand the nature of the study and its procedures, and the patient is expected to complete the study as designed.
7. For a patient who is a minor, the parent(s)/legal guardian(s) provides written informed consent, and the patient provides assent (in accordance with local regulations). Adult patients (in accordance with local regulations) provide their own written informed consent.
8. A caregiver provides written informed consent after being assigned the role by an adult patient or if this role is delegated by the parent/legal guardian of a patient who is a minor.
9. Females who are postmenarchal or ≥12 years of age may be included only if they have a negative β-HCG test on day 1 or are sterile.
10. Females who are postmenarchal or ≥12 years of age whose male partners are potentially fertile (i.e., no vasectomy) must use highly effective birth control methods for the duration of the study (i.e., starting at day 1) and for 30 days after last dose of deutetrabenazine.

Patients will be excluded from participating in this study if they meet any of the following criteria:
1. Patient has clinically significant depression at day 1 of this study.
2. Patient has a history of suicidal intent or related behaviors:
   previous intent to act on suicidal ideation with a specific plan, irrespective of level of ambivalence, at the time of suicidal thought
3. Patient has a history of a previous actual, interrupted, or aborted suicide attempt.
4. Patient has a first-degree relative who has completed suicide.
5. Patient who is currently receiving or who has received botulinum neurotoxin (BoNT) in an investigational clinical trial.
6. Patient has received any of the following concomitant medications for dystonia or chorea within the specified exclusionary windows of day 1 of this study:
   within 3 months: depot neuroleptics
   within 30 days: tetrabenazine or valbenazine
   within 21 days: reserpine
   within 14 days: neuroleptics (oral), typical and atypical antipsychotics, metoclopramide, levodopa, dopamine agonists, and monoamineoxidase inhibitors
7. Patient has received treatment with stem cells, deep brain stimulation, transmagnetic stimulation, or transcranial direct current stimulation for treatment of abnormal movements or CP, or the patient is not in a stable clinical condition.
8. Patient has recent surgical procedure or is anticipated to have a surgical procedure during the study that, in the opinion of the investigator, makes the patient unsuitable for the study.
9. Patient has a severe mental disability or an unstable or serious medical illness (e.g., epilepsy) that, in the opinion of the investigator, could jeopardize or would compromise the patient's ability to participate in this study.
10. Patient has a QT interval (QTc) corrected for heart rate using Fridericia's formula (QTcF) value >450 msec on 12-lead ECG at day 1 of this study.
11. Patients with a history of torsade de pointes, congenital long QT syndrome, bradyarrhythmias, other cardiac arrhythmias, or uncompensated heart failure.
12. Patient has evidence of hepatic impairment, as indicated by the following:
    aspartate aminotransferase (AST) or alanine aminotransferase (ALT) >2.5× the upper limit of the normal range (ULN) at day 1 of this study
    alkaline phosphatase (ALP) or total bilirubin (Tbil) >2×ULN at day 1 of this study
13. Patient has evidence of clinically significant renal impairment, indicated by a serum creatinine >1.5×ULN at day 1 of this study.
14. Patient has a known allergy to any of the components of deutetrabenazine.
15. Patient has participated in an investigational drug or device study other than the parent Study and received IMP/intervention within 30 days or 5 drug half-lives of day 1 of this study, whichever is longer.
16. Patient is pregnant or breastfeeding.
17. Patient has a history of or acknowledges alcohol or substance abuse, as defined in the Diagnostic and Statistical Manual of Mental Disorders, Fifth Edition (DSM-V™).
18. Patient has a positive urine drug screen test result or is unable to refrain from substance abuse throughout the study.

Results

Long term administration of tolerable amounts of deutetrabenazine is shown to reduce abnormal involuntary movements associated with dyskinesia in cerebral palsy with a favorable safety profile.

Example 3: Efficacy Study in Adults

A Phase 3 study to evaluate the efficacy and safety of deutetrabenazine is performed on a population consisting of male and female patients, diagnosed with DCP. Patients may be included in the study only if they meet all of the following criteria:
1. Patient is older than 18 years of age at baseline.
2. Patient has had cerebral palsy (CP) symptoms since infancy (≤2 years).
3. Patient has a diagnosis of DCP according to the Surveillance of Cerebral Palsy in Europe criteria.
4. Patient has a total score of ≥10 on the MD-CRS part II items at the baseline visit, based on investigator scoring of chorea.
5. Patient's symptoms are causing functional problems determined by a Clinical Global
Impression of Severity (CGI-S) score of 4 or greater based on investigator scoring.
6. Choreiform is the predominant movement disorder as assessed by the EAB at screening.

Patients will receive 6 mg to 48 mg of deutetrabenazine. The titration scheme and maximum dose follows the one in the parent study, Example 1, supra.

Results

Administration of tolerable amounts of deutetrabenazine to adult patients is shown to reduce abnormal involuntary movements associated with dyskinesia in cerebral palsy with a favorable safety profile.

Example 4: Efficacy Study

A Phase 3 study to evaluate the efficacy and safety of deutetrabenazine is performed on a population consisting of male and female patients, diagnosed with DCP. Patients may be included in the study only if they meet all of the following criteria:
1. Patient is 6 through 18 years of age (inclusive) at baseline.
2. Patient has had cerebral palsy (CP) symptoms since infancy (≤2 years).
3. Patient has a diagnosis of DCP according to the Surveillance of Cerebral Palsy in Europe criteria.
4. Patient has a total score of ≥10 on the MD-CRS part II items at the baseline visit, based on investigator scoring of chorea.
5. Patient's symptoms are causing functional problems determined by a Clinical Global
Impression of Severity (CGI-S) score of 4 or greater based on investigator scoring.
6. Patient's predominant motor symptoms are dystonic.

Patients will receive 6 mg to 48 mg of deutetrabenazine. The titration scheme and maximum dose follows the one in the parent study, Example 1, supra.

Results

Administration of tolerable amounts of deutetrabenazine to pediatric patients is shown to reduce dystonic abnormal involuntary movements associated with dyskinesia in cerebral palsy with a favorable safety profile.

Those skilled in the art will appreciate that numerous changes and modifications can be made to the preferred embodiments of the disclosure and that such changes and modifications can be made without departing from the spirit of the disclosure. It is, therefore, intended that the appended claims cover all such equivalent variations as fall within the true spirit and scope of the disclosure.

What is claimed:

1. A method of treating dyskinesia in cerebral palsy in a human patient in need of treatment thereof comprising administering to the patient about 6 mg/day to about 48 mg/day, in one or two doses, of a compound having Formula (I):

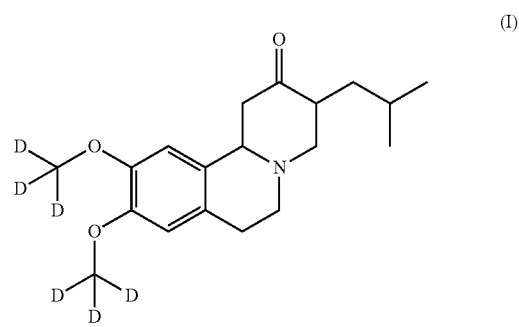

or pharmaceutically acceptable salt thereof, wherein each position represented as D has deuterium enrichment of no less than about 10%;
wherein the treating results in maintaining or reducing abnormal involuntary movements associated with dyskinesia in cerebral palsy in the patient, relative to the patient's abnormal involuntary movements at baseline.

2. The method of claim 1, wherein the abnormal involuntary movements associated with dyskinesia in cerebral palsy are of dystonic type.

3. The method of claim 1, wherein the abnormal involuntary movements associated with dyskinesia in cerebral palsy are of choreiform type.

4. The method of claim 1, wherein the human patient is a pediatric patient.

5. The method of claim 1, wherein the abnormal involuntary movements associated with dyskinesia in cerebral palsy are measured by at least one of the rating scales:
a) the MD-CRS part II;
b) the MD-CRS part I;
c) the CaGI-I; and
d) the CGI-I.

6. The method of claim 5, wherein the abnormal involuntary movements associated with dyskinesia in cerebral palsy are reduced by at least 20% relative to the patient's abnormal involuntary movements at baseline.

7. The method of claim 5, wherein the patient exhibits a reduction in the MD-CRS part II total score of at least 0.5 points, relative to baseline.

8. The method of claim 5, wherein the patient exhibits a reduction in the MD-CRS part I total score of at least 2 points, relative to baseline.

9. The method of claim 1, wherein the patient weighs at least 12 kg at baseline.

10. The method of claim 9, wherein the patient weighs 12 kg to <17 kg at baseline and wherein the daily amount of deutetrabenazine administered is less than or equal to about 24 mg if the patient does not have a CYP2D6 impairment; or less than or equal to about 12 mg if the patient has a CYP2D6 impairment.

11. The method of claim 9, wherein the patient weighs 17 kg to <30 kg at baseline and wherein the daily amount of deutetrabenazine administered is less than or equal to about 30 mg if the patient does not have a CYP2D6 impairment; or less than or equal to about 18 mg if the patient has a CYP2D6 impairment.

12. The method of claim 9, wherein the patient weighs 30 kg to <40 kg at baseline and wherein the daily amount of deutetrabenazine administered is less than or equal to about 42 mg if the patient does not have a CYP2D6 impairment; or less than or equal to about 24 mg if the patient has a CYP2D6 impairment.

13. The method of claim 9, wherein the patient weighs ≥40 kg at baseline and wherein the daily amount of deutetrabenazine administered is less than or equal to about 48 mg if the patient does not have a CYP2D6 impairment; or less than or equal to about 36 mg if the patient has a CYP2D6 impairment.

14. The method of claim 1, wherein each position represented as D has deuterium enrichment of no less than about 50%, no less than about 90%, no less than about 95%, no less than about 98%, or no less than about 99%.

15. A method of treating dyskinesia in cerebral palsy in a human patient in need thereof comprising administering to the patient about 6 mg/day to about 48 mg/day, in one or two doses of a compound having the Formula (II):

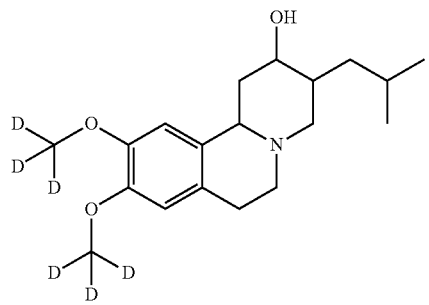

or pharmaceutically acceptable salt thereof, wherein each position represented as D has deuterium enrichment of no less than about 10%;

wherein the treating results in maintaining or reducing abnormal involuntary movements associated with dyskinesia in cerebral palsy in the patient, relative to the patient's abnormal involuntary movements at baseline.

16. The method of claim 15, wherein each position represented as D has deuterium enrichment of no less than about 50%, no less than about 90%, no less than about 95%, no less than about 98%, or no less than about 99%.

* * * * *